United States Patent
Sluka et al.

(10) Patent No.: US 8,518,902 B2
(45) Date of Patent: Aug. 27, 2013

(54) USE OF RNAI TECHNOLOGY TO INHIBIT ASIC3

(75) Inventors: Kathleen A. Sluka, Coralville, IA (US); Roxanne Y. Walder, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 145 days.

(21) Appl. No.: 13/017,738

(22) Filed: Jan. 31, 2011

(65) Prior Publication Data

US 2011/0237645 A1    Sep. 29, 2011

Related U.S. Application Data

(60) Provisional application No. 61/300,311, filed on Feb. 1, 2010.

(51) Int. Cl.
| | |
|---|---|
| *C07H 21/02* | (2006.01) |
| *C07H 21/04* | (2006.01) |
| *A61K 31/70* | (2006.01) |
| *C12Q 1/68* | (2006.01) |

(52) U.S. Cl.
USPC ...... 514/44 A; 514/44 R; 536/23.1; 536/24.1; 536/24.5

(58) Field of Classification Search
None
See application file for complete search history.

(56) References Cited

U.S. PATENT DOCUMENTS

| 7,838,005 B2 * | 11/2010 | Chen et al. | 424/198.1 |
|---|---|---|---|
| 2005/0267009 A1 * | 12/2005 | Deagle | 514/2 |
| 2007/0281986 A1 * | 12/2007 | Collier et al. | 514/403 |
| 2008/0146502 A1 * | 6/2008 | Collier et al. | 514/12 |

OTHER PUBLICATIONS

Sluka, Kathleen A. et al., "ASIC3 in muscle mediates mechanical, but not heat, hyperalgesia associated with muscle inflammation", Pain 129 (2007), pp. 102-112.
Sluka, Kathleen A. et al., "Chronic hyperalgesia induced by repeated acid injections in muscle is abolished by the loss of ASIC3, but not ASIC1", Pain 106 (2003), pp. 229-239.
Walder, R. Y. et al., "ASIC1 and ASIC3 Play Different Roles in the Development of Hyperalgesia Following Inflammatory Muscle Injury", J. Pain, Mar. 2010; 11(3):210-218.
Walder, R. Y. et al., "Selective Targeting of ASIC3 Using miRNAs Results in the Inhibition of Primary and Secondary Hyperalgesia in Mice", Brochure Supported by the National Intsitutes of Health AR053509, Jan. 24, 2011, 1 page.
Walder, R. Y. et al., "Selective targeting of ASIC3 using artificial miRNAs inhibits primary and secondary hyperalgesia after muscle inflammation", Pain 152 (2011), pp. 2348-2356.

* cited by examiner

*Primary Examiner* — Sean McGarry
(74) *Attorney, Agent, or Firm* — McKee, Voorhees & Sease, P.L.C.

(57) ABSTRACT

In vitro studies using cells transfected with acid-sensing ion channel 3 (ASIC3) or acid-sensing ion channel 1 (ASIC1) cDNA, demonstrated that the miRNAs against mouse ASIC3 (miR844 and miR847) selectively inhibit mouse ASIC3, but not ASIC1 as detected by protein expression and responses to pH. When the RNAi agents, miR844 or miR847, were used in vivo, delivered into the muscle of mice using a replication-defective herpes simplex viral (HSV-1) vector, primary and secondary hyperalgesia were reduced after carrageenan-induced muscle inflammation. Accordingly, the present invention provides RNAi agents that target ASIC3, methods of preparing such RNAi agents, and methods of using them to modulate in a cell the level of ASIC3 or activity of an ASIC including at least one ASIC3. Modulation of ASIC3 activity or levels can be used for different purposes such as treating pain associated with the expression of ASIC3 and the like.

3 Claims, 20 Drawing Sheets

Anneal the top and bottom 844 oligonucleotides

Mmi513844 top
TGCTGTGAAGTTCTCAGGTCCACAGGGTTTTGGCCACTGACTGACCCTGTGGATGAGAACTTCA
      CACTTCAAGAGTCCAGGTGTCCCAAAACCGGTGACTGACTGGGACACCTACTCTCTTGAAGTGTCC
Mmi513844 bottom

FIG. 9

Insert 513844 into
pcDNA6.2-GW/EmGFP-miR

Mmi513844 top

TGCTGTGAAGTTCTCAGGTCCACAGGGTTTGGCCACTGACTGACCCTGTGGATGAGAACTTCA
CACTTCAAGAGTCCAGGTGTCCCAAAACCGGTGACTGACTGGGACACCTACTCTTGAAGTGTCC

Mmi513844 bottom

Synthetic Oligonucleotides for Cloning Mouse 847 ASIC3 miRNA

Mmi 513847 top
TGCTGTACACAAAGTGACAGCTGGGAGTTTTGGCCACTGACTGACTCCCAGCTCACTTTGTGTA

Mmi 513847 bottom
CCTGTACACAAAGTGAGCTGGGAGTCAGTCAGTGGCCAAAACTCCCAGCTGTCACTTTGTGTAC

FIG. 13

Synthetic Oligonucleotides for Cloning Human ASIC3 miRNA

Hsa844 analog top
TGCTGTGTGAAGTTCTCAGGCCCACAAGGTTTTGGCCACTGACTGACCTGTGGGTGAGAACTTCA Hsa844 analog bottom
CCTGTGAAGTTCTCACCCACAAGGTCAGTCAGTGGCCAAAACCTTGTGGGCCTGAGAACTTCAC Hsa847 analog top
TGCTGTGCACAGGGTGACAGCGGGAGTTTTGGCCACTGACTGACTCCCGGCTCACCCTGTGCA Hsa847 analog bottom
CCTGTGCACAGGGTGAGCCGGGAGTCAGTCAGTGGCCAAAACTCCCGCTGTCACCCTGTGCAC

FIG. 14

Table 2: miRNA Targets for ASIC3

| miRNA | Antisense Sequence | ASIC3 Target* |
|---|---|---|
| 844 | TGAAGTTCTCAGGTCCACAGGG | 510-531 |
| 847 | TACACAAAGTGACACAGCTGGGA | 259-279 |
| Hu844 | TGAAGTTCTCAGGCCCACAAGG | 507-528 |
| Hu847 | TGCACAGGGTGACAGCCGGGA | 256-276 |

*based on the distance from the CDS start; NM_183000 (mouse) and NM_004769 (human)

FIG. 15

SEQUENCE LISTING

<160> NUMBER OF SEQ ID NOS: 27

<210> SEQ ID NO 1
<211> LENGTH: 64
<212> TYPE: DNA
<213> ORGANISM: Mus musculus

<400> SEQUENCE: 1
tgctgtgaag ttctcaggtc cacagggttt tggccactga ctgaccctgt ggatgagaac    60
ttca                                                                 64

<210> SEQ ID NO 2
<211> LENGTH: 64
<212> TYPE: DNA
<213> ORGANISM: Mus musculus

<400> SEQUENCE: 2
cctgtgaagt tctcatccac agggtcagtc agtggccaaa accctgtgga cctgagaact    60
tcac                                                                 64

<210> SEQ ID NO 3
<211> LENGTH: 128
<212> TYPE: DNA
<213> ORGANISM: Mus musculus

<400> SEQUENCE: 3
tgctgtgaag ttctcaggtc cacagggttt tggccactga ctgaccctgt ggatgagaac    60
ttcacacttc aagagtccag gtgtcccaaa accggtgact gactgggaca cctactcttg   120
aagtgtcc                                                            128

<210> SEQ ID NO 4
<211> LENGTH: 22
<212> TYPE: DNA
<213> ORGANISM: Mus musculus

<400> SEQUENCE: 4
gaagttctca ggtccacagg gt                                             22

<210> SEQ ID NO 5
<211> LENGTH: 21
<212> TYPE: DNA
<213> ORGANISM: Mus musculus

<400> SEQUENCE: 5
cuucaagagu ccaggtctcc c                                              21

<210> SEQ ID NO 6
<211> LENGTH: 64
<212> TYPE: DNA
<213> ORGANISM: Mus musculus

<400> SEQUENCE: 6
tgctgtacac aaagtgacag ctgggagttt tggccactga ctgactccca gctcactttg    60
tgta                                                                 64

<210> SEQ ID NO 7
<211> LENGTH: 64
<212> TYPE: DNA
<213> ORGANISM: Mus musculus

<400> SEQUENCE: 7
cctgtacaca aagtgagctg ggagtcagtc agtggccaaa actcccagct gtcactttgt    60
gtac                                                                64

<210> SEQ ID NO 8
<211> LENGTH: 21
<212> TYPE: DNA
<213> ORGANISM: Mus musculus

<400> SEQUENCE: 8
tacacaaagt gacagctggg a                                              21

<210> SEQ ID NO 9
<211> LENGTH: 64
<212> TYPE: DNA
<213> ORGANISM: Homo sapiens

<400> SEQUENCE: 9
tgctgtgaag ttctcaggcc cacaaggttt tggccactga ctgaccttgt gggtgagaac    60
ttca                                                                64

<210> SEQ ID NO 10
<211> LENGTH: 64
<212> TYPE: DNA
<213> ORGANISM: Homo sapiens

<400> SEQUENCE: 10
cctgtgaagt tctcacccac aaggtcagtc agtggccaaa accttgtggg cctgagaact    60
tcac                                                                64

<210> SEQ ID NO 11
<211> LENGTH: 22
<212> TYPE: DNA
<213> ORGANISM: Homo sapiens

<400> SEQUENCE: 11
tgaagttctc aggcccacaa gg                                             22

<210> SEQ ID NO 12
<211> LENGTH: 64
<212> TYPE: DNA
<213> ORGANISM: Homo sapiens

<400> SEQUENCE: 12
tgctgtgcac agggtgacag ccgggagttt tggccactga ctgactcccg gctcaccctg    60
tgca                                                                64

<210> SEQ ID NO 13
<211> LENGTH: 64
<212> TYPE: DNA
<213> ORGANISM: Homo sapiens

<400> SEQUENCE: 13
cctgtgcaca gggtgagccg ggagtcagtc agtggccaaa actcccggct gtcaccctgt    60
gcac                                                                64

<210> SEQ ID NO 14
<211> LENGTH: 21
<212> TYPE: DNA
<213> ORGANISM: Homo sapiens

<400> SEQUENCE: 14
tgcacagggt gacagccggg a    21

<210> SEQ ID NO 15
<211> LENGTH: 1978
<212> TYPE: DNA
<213> ORGANISM: Mus musculus

<400> SEQUENCE: 15

```
cagagaccca gccccacgga gtcaacgcct gttctgggga aggcagagct gaccgaagtt      60
caactcatcc agtcctatca ggccagtact ttcacctgtc ttggctcctc ccgtctctac     120
cttctccttc tctctccgta ttccttgctg agctacttga gtcccatttc aatccccacc     180
actatcctgc tagccctaca aaacagcttc cgtgctcctt agaaatccca tccccagtca     240
ggaaacctcc ctgctccagc catgaaacct ccctcaggac tggaggaggc ccagcggcga     300
caggcctcag acatccgggt gttcgccaac agctgcacga tgcatggttt gggccacatc     360
tttggccctg gaggcctgac cctgcgccgt gggctgtggg ccacagctgt actcctgtcg     420
ctggcggcct tcctctacca ggtggctgag cgggttcgct actatgggga gttccaccat     480
aagaccaccc tggatgagcg tgagagccac cagcttacct tcccagctgt cactttgtgt     540
aacatcaatc cctgcgccg ctcacgcctc acacccaatg acttgcactg gccggaacg      600
gcactgctgg gtctggaccc tgctgaacat gctgcctacc ttcgtgccct gggccagccc     660
cctgcaccac ctggcttcat gcccagtccg acttttgaca tggcacaact ctacgccaga     720
gccggccact cccttgagga catgttgctg gactgccgat accgtggcca gccctgtgga     780
cctgagaact tcacagtgat tttcactcga atggggcaat gctacacctt caactctggt     840
gcccagggg cagagctgct caccactcct aagggcggtg ctggcaatgg actggagatt     900
atgctggatg tacagcagga ggagtatctg cccatctgga aggacatgga agagacccca     960
tttgaggtgg ggatccgagt gcagatccac ggccaggagg aaccccctgc cattgaccag    1020
ctgggcttcg gtgctgcccc aggccaccag acttttgtgt cctgccagca acagcaactg    1080
agtttcctgc caccacctg gggtgactgc aataccgcat ctgtggatcc cgactttgat    1140
ccagagccct ctgatcccct gggttcccct agctccagcc ctccttatag cttaatagggg   1200
tgtcgcctgg cctgtgagtc acgctatgtg gctcggaagt gcggatgtcg aatgatgcat    1260
atgcctggaa actccccagt gtgcagcccc cagcagtaca aggactgtgc cagcccagct    1320
ctggacgcta tgctgcgaaa ggacacttgt gtctgtccca cccgtgcgc cactacacgc     1380
tatgccaagg agctctccat ggtgcggatt cccagccgcg cttcagctcg ctacctggcc    1440
cggaaataca accgtagcga gacttacatc acggagaatg tactggttct ggatatcttc    1500
tttgaagccc tcaactatga ggccgtggaa caaaaggcag cttatgaagt gtcggagttg    1560
ctgggagaca ttgggggaca gatgggactg tttatcggag ccagcctgct taccatcctc    1620
gagatcctcg actacctctg tgaggttttt caagacagag tcctgggggta cttctggaac    1680
agaaggagct ctcaaaggcg ctctggcaac actctgctcc aggaagagtt gaatgggcat    1740
cgaacacatg ttccccatct cagcctaggc cccaggcctc ctaccgctcc cagtgctgtc    1800
accaagacac tcgctgcctc ccaccgtacc tgttacctcg tgacaaggct ctagacctgc    1860
ttggctgcgc cgtgacatct tggacatgcc caggctgtac atctttgcct tctttaccct    1920
aataaagctc tagtacacgt gcaaaaaaaa aaaaaaaaaa aaaaaaaaaa aaaaaaaa      1978
```

<210> SEQ ID NO 16

<211> LENGTH: 2068
<212> TYPE: DNA
<213> ORGANISM: Homo sapiens

<400> SEQUENCE: 16

```
ctgaaaccca atcctctgca gcagcgccgg ctcagcaccg ccggctcagc accgctccgc      60
agcccctgcc tgccacggtc agctacgtcc cacctggtct gctgcggagt ccccagccca     120
gtgcctagcc cagtggagcc accgcctgtt cctcgggaag gaacagtggg acctgaccgg     180
ccagatcacc tcctccaatc ctgccaggct agtgcctccc tgccttccaa ccttggctgt     240
ctcccaccct ctcttctcct ctccttgcct ggcctcctga atcctatctt agcctcctta     300
gccccctgac tgactctctc tcgcttcttc caagcctctg tagctggttc cgctcctggg     360
ttctggccat gaagcccacc tcaggcccag aggaggcccg gcggccagcc tcggacatcc     420
gcgtgttcgc cagcaactgc tcgatgcacg ggctgggcca cgtcttcggg ccaggcagcc     480
tgagcctgcg ccggggggatg tgggcagcgg ccgtggtcct gtcagtgcc accttcctct      540
accaggtggc tgagagggtg cgctactaca gggagttcca ccaccagact gccctggatg     600
agcgagaaag ccaccggctc atcttccgg ctgtcaccct gtgcaacatc aacccactgc      660
gccgctcgcg cctaacgccc aacgacctgc actgggctgg gtctgcgctg ctgggcctgg     720
atcccgcaga gcacgccgcc ttcctgcgcg ccctgggccg gccccctgca ccgcccggct     780
tcatgcccag tcccaccttt gacatggcgc aactctatgc ccgtgctggg cactccctgg     840
atgacatgct gctggactgt cgcttccgtg gccaaccttg tgggcctgag aacttcacca     900
cgatcttcac ccggatggga aagtgctaca catttaactc tggcgctgat ggggcagagc     960
tgctcaccac tactaggggt ggcatgggca atgggctgga catcatgctg acgtgcagc    1020
aggaggaata tctacctgtg tggagggaca atgaggagac cccgtttgag gtggggatcc    1080
gagtgcagat ccacagccag gaggagccgc ccatcatcga tcagctgggc ttggggtgt    1140
cccgggcta ccagaccttt gtttcttgcc agcagcagca gctgagcttc ctgccaccgc    1200
cctgggcga ttgcagttca gcatctctga accccaacta tgagccagag ccctctgatc    1260
ccctaggctc ccccagcccc agcccagcc ctccctatac ccttatgggg tgtcgcctgg     1320
cctgcgaaac ccgctacgtg gctcggaagt gcggctgccg aatggtgtac atgccaggcg    1380
acgtgccagt gtgcagcccc cagcagtaca agaactgtgc ccaccgcc atagatgcca     1440
tgcttcgcaa ggactcgtgc gcctgcccca accgtgcgc cagcacgcgc tacgccaagg     1500
agctctccat ggtgcggatc ccgagccgcg ccgccgcgcg cttcctggcc cggaagctca    1560
accgcagcga ggcctacatc gcggagaacg tgctggccct ggacatcttc tttgaggccc    1620
tcaactatga gaccgtggag cagaagaagg cctatgagat gtcagagctg cttggtgaca    1680
ttgggggcca gatggggctg ttcatcgggg ccagcctgct caccatcctc gagatcctag    1740
actacctctg tgaggtgttc cgagacaagg tcctgggata tttctggaac cgacagcact    1800
cccaaaggca ctccagcacc aatctgcttc aggaagggct gggcagccat cgaacccaag    1860
ttccccacct cagcctgggc cccagacctc ccacccctcc ctgtgccgtc accaagactc    1920
tctccgcctc ccaccgcacc tgctaccttg tcacacagct ctagacctgc tgtctgtgtc    1980
ctcggagccc cgccctgaca tcctggacat gcctagcctg cacgtagctt ttccgtcttc    2040
accccaaata aagtcctaat gcatcagc                                       2068
```

<210> SEQ ID NO 17
<211> LENGTH: 21
<212> TYPE: RNA

<213> ORGANISM: Mus musculus

<400> SEQUENCE: 17
cuucaagagu ccaggugucc c                                              21

<210> SEQ ID NO 18
<211> LENGTH: 21
<212> TYPE: RNA
<213> ORGANISM: Mus musculus

<400> SEQUENCE: 18
auguguuuca cugucgaccc u                                              21

<210> SEQ ID NO 19
<211> LENGTH: 21
<212> TYPE: RNA
<213> ORGANISM: Homo sapiens

<400> SEQUENCE: 19
acguguccca cugucggccc u                                              21

<210> SEQ ID NO 20
<211> LENGTH: 22
<212> TYPE: RNA
<213> ORGANISM: Homo sapiens

<400> SEQUENCE: 20
acuucaagag uccggguguu cc                                             22

<210> SEQ ID NO 21
<211> LENGTH: 22
<212> TYPE: DNA
<213> ORGANISM: Homo sapiens

<400> SEQUENCE: 21
tgaagttctc aggtccacag gg                                             22

<210> SEQ ID NO 22
<211> LENGTH: 64
<212> TYPE: DNA
<213> ORGANISM: Homo sapiens

<400> SEQUENCE: 22
tgctgtgggc atgaagccag gtggtggttt tggccactga ctgaccacca cctcttcatg   60
ccca                                                                 64

<210> SEQ ID NO 23
<211> LENGTH: 63
<212> TYPE: DNA
<213> ORGANISM: Homo sapiens

<400> SEQUENCE: 23
cctgtgggca tgaagaggtg gtggtcagtc agtggccaaa accaccacct ggcttcatgc   60
cac                                                                  63

<210> SEQ ID NO 24
<211> LENGTH: 21
<212> TYPE: RNA
<213> ORGANISM: Homo sapiens

<400> SEQUENCE: 24
caccaccugg cuucaugccc a                                              21

```
<210> SEQ ID NO 25
<211> LENGTH: 64
<212> TYPE: DNA
<213> ORGANISM: Homo sapiens

<400> SEQUENCE: 25
tgctgaaacc atgcatcgtg cagctggttt tggccactga ctgaccagct gcaatgcatg      60
gttt                                                                   64

<210> SEQ ID NO 26
<211> LENGTH: 64
<212> TYPE: DNA
<213> ORGANISM: Homo sapiens

<400> SEQUENCE: 26
cctgaaacca tgcattgcag ctggtcagtc agtggccaaa accagctgca cgatgcatgg      60
tttc                                                                   64

<210> SEQ ID NO 27
<211> LENGTH: 21
<212> TYPE: RNA
<213> ORGANISM: Homo sapiens

<400> SEQUENCE: 27
cagcugcacg augcaugguu u                                                21
```

USE OF RNAI TECHNOLOGY TO INHIBIT ASIC3

CROSS-REFERENCE TO RELATED APPLICATIONS

This application claims priority under 35 U.S.C. §119 to provisional application Ser. No. 61/300,311 filed Feb. 1, 2010, herein incorporated by reference in its entirety.

GRANT REFERENCE

This invention was made with government support under 1RO1NS048936-01 and AR053509 (KAS) awarded by the National Institutes of Health. The government has certain rights in the invention.

BACKGROUND OF THE INVENTION

Acid-sensing ion channels (ASICs) are proton-gated voltage-independent ion channels located on neurons in the peripheral and central nervous systems. ASICs are also found in non-neuronal cells like muscle cells, synoviocytes, and bone cells. ASICs belong to the epithelial sodium channel/ degenerin (ENaC/DEG) family of amiloride-sensitive transmembrane ion channel proteins (see[37, 41, 78]). Four genes within mammalian genomes encode seven subunits to date— ASIC1a, ASIC1b, ASIC1b2, ASIC2a, ASIC2b, ASIC3 and ASIC4.[1, 15, 26, 27, 40, 54, 69, 73] Homomeric and heteromeric ASIC subunits combine to form trimeric ASICs,[13, 34] which depending on the subunit composition in the DRG display differences in pH sensitivity, current kinetics and ion selectivity.[11, 20, 29, 53] ASICs respond to acidosis, play a significant role in nociceptive processing of hyperalgesia both peripherally and centrally.[1, 3, 6, 8-10, 15, 16, 21, 27, 28, 37, 40-42, 54, 65, 66, 68, 70, 72-74, 76]

Illness or trauma can often lead to decreases in pH which activate ASICs. The tissue acidosis associated with inflammation, infection, and ischemia causes pain (Reeh, P. W., and Steen, K. H. (1996). Tissue acidosis in nociception and pain. Prog Brain Res 113, 143-151). Acidosis also generates proton-dependent transient and sustained $Na^{30}$ currents in cultured sensory neurons (Bevan, S., and Yeats, J. (1991). Protons activate a cation conductance in a sub-population of rat dorsal root ganglion neurons. J Physiol (Lond) 433, 145-161; Davies, N. W., Lux, H. D., and Morad, M. (1988). Site and mechanism of activation of proton-induced sodium current in chick dorsal root ganglion neurons. J Physiol (Lond) 400, 159-187).

Pain is a common ailment. For example, pain such as musculoskeletal pain affects the great majority of the population, and nearly half of the population suffers from chronic musculoskeletal pain. Currently available treatments are inadequate to treat most chronic pain conditions. Therefore, for these and other reasons there is a need for a safe treatment of pain that could be safe and used in long-term modalities.

BRIEF SUMMARY OF THE INVENTION

The present invention relates to compositions and methods for decreasing expression and/or activity of acid-sensing ion channel 3 (ASIC3) using one or more RNAi agents targeted to a transcript that encodes ASIC3. Accordingly, such agents are useful in methods of treating or preventing a disease, disorder or condition associated with ASIC3 expression or activity. The RNAi agents may be used to treat or prevent a disease, disorder or condition associated with or mediated by a decrease in extracellular pH. These methods include administering to a subject in need thereof an effective amount of the RNAi agent for a sufficient amount of time to obtain a desired response.

Also provided herein are methods of decreasing expression or activity of ASIC3 in a cell. The method includes contacting the cell ASIC3 with an effective amount of a RNAi agent targeted to a transcript that encodes ASIC3. The RNAi agent and cell are in contact for a sufficient amount of time for a decrease in ASIC3 expression and/or activity to occur.

Therefore it is a primary object feature or advantage of the present invention to improve over the state of the art.

A further object, feature, or advantage of the invention is to use RNA interference (RNAi) to target the expression or activity of acid-sensing ion channel 3 (ASIC3).

A further object, feature, or advantage of the invention is to selectively inhibit ASIC3.

Another object, feature, or advantage of the invention is to provide methods and compositions to reduce or treat pain.

Yet another object, feature, or advantage of the invention is to provide methods and compositions to treat diseases, disorders, or conditions associated with ASIC3 expression or activity.

An object, feature, or advantage of the present invention is to provide methods and compositions to treat diseases, disorders, or conditions associated with an increase in extracellular pH.

It is a further object, feature, or advantage of the present invention to provide methods and compositions for short-term treatment of pain.

Yet another object, feature, or advantage of the invention is to provide methods and compositions for long-term treatment of pain.

Still another object, feature, or advantage of the invention is to provide methods and compositions for treating primary hyperalgesia.

An object, feature, or advantage of the present invention is to provide methods and compositions for treating secondary hyperalgesia.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 9 shows the DNA sequence of the two synthetic oligonucleotides that were used to clone miRNA844. The top and bottom oligonucleotides as annealed.

FIG. 13 shows the DNA sequence for the two synthetic oligonucleotides for cloning Mouse 847 ASIC3 miRNA.

FIG. 14 shows synthetic oligonucleotides for cloning Human ASIC3 miRNA.

FIG. 15 shows a table (Table 2) summarizing the antisense sequences, and the nucleotide location for the various miRNA targets on mouse or human ASIC3 mRNA.

BRIEF DESCRIPTION OF THE SEQUENCES

Figure 1:
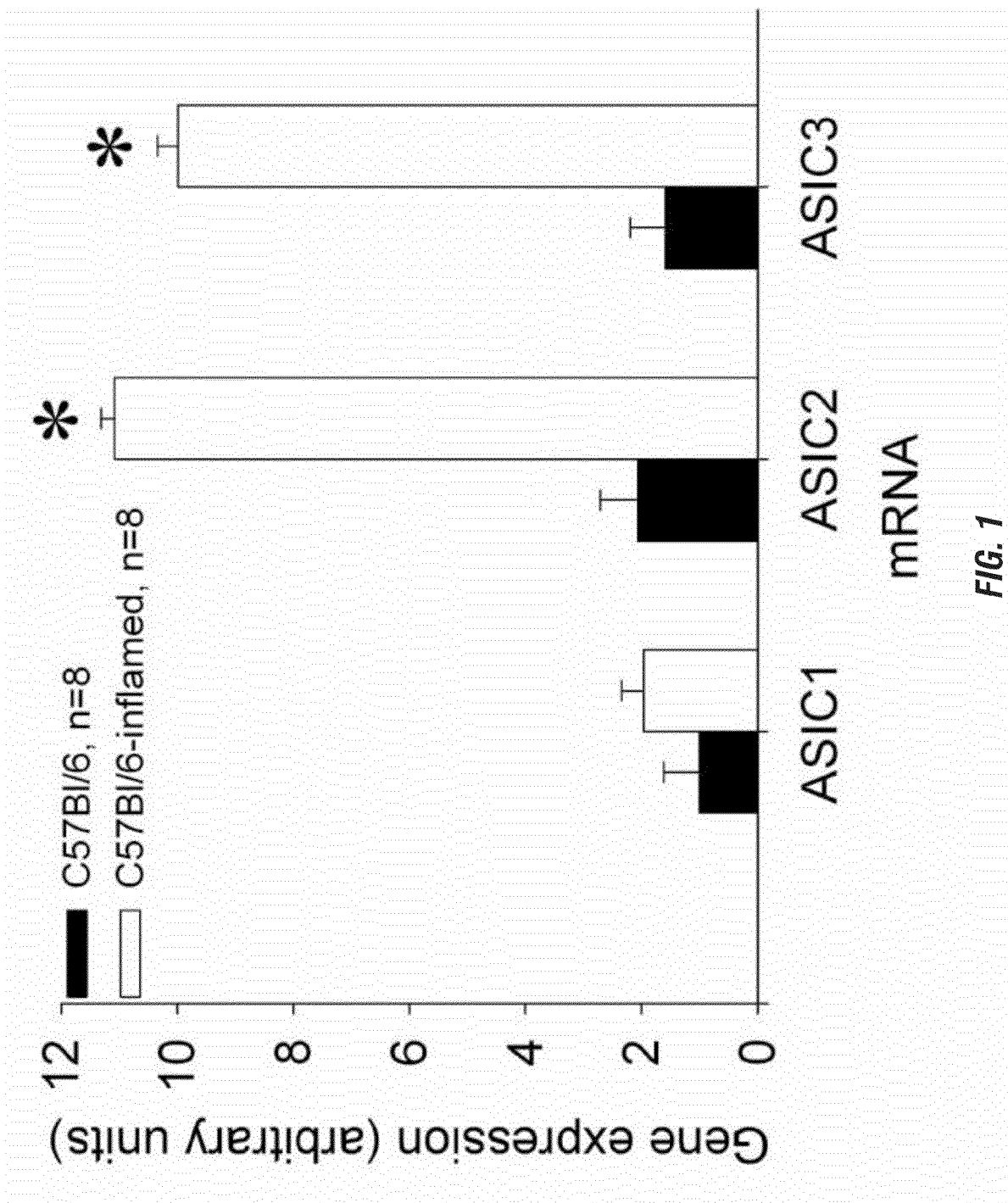
FIG. 1. shows comparative qRT-PCR analysis for ASIC1, ASIC2, and ASIC3 mRNAs of L4, L5, and L6 DRGs from C57Bl/6 versus C57Bl/6-inflamed mice. There are bilateral increases in ASIC2 and ASIC3, and not ASIC1 mRNA levels, 24 hours after muscle inflammation. No differences were measured between the ipsilateral and contralateral mRNAs. (*=significantly greater than uninflamed mice, P<0.05).

The application provides details of sequences as shown in Table 1 below.

TABLE 1

| SEQ ID NO: | Polynucleotide (pnt) | RNA or DNA | Length | Identification |
|---|---|---|---|---|
| 1 | pnt | DNA | 64 | Synthetic oligonucleotide for cloning miRNA844-top strand |
| 2 | pnt | DNA | 64 | Synthetic oligonucleotide for cloning miRNA844-bottom strand |
| 3 | pnt | DNA | 64 | the two synthetic oligonucleotides for cloning miRNA844 annealed (sequences 1 and 2 annealed) |
| 4 | pnt | DNA | 22 | the DNA sequence of the active moiety of miRNA 844 |
| 5 | pnt | RNA | 21 | The target sequence of miRNA844 on ASIC3 mRNA |
| 6 | pnt | DNA | 64 | Synthetic oligonucleotide for cloning miRNA847-top strand |
| 7 | pnt | DNA | 64 | Synthetic oligonucleotide for cloning miRNA847-bottom strand |
| 8 | pnt | DNA | 21 | the DNA sequence of the active moiety of miRNA 847 |
| 9 | pnt | DNA | 64 | Synthetic oligonucleotide for cloning human miRNA844-top strand |
| 10 | pnt | DNA | 64 | Synthetic oligonucleotide for cloning human miRNA844-bottom strand |
| 11 | pnt | DNA | 22 | the DNA sequence of the active moiety of human miRNA 844 |
| 12 | pnt | DNA | 64 | Synthetic oligonucleotide for cloning human miRNA847-top strand |
| 13 | pnt | DNA | 64 | Synthetic oligonucleotide for cloning human miRNA847-bottom strand |
| 14 | pnt | DNA | 21 | the DNA sequence of the active moiety of human miRNA 847 |
| 15 | pnt | DNA | 1978 | Mouse ASIC3 Genbank Accession No NM_183000 |
| 16 | pnt | DNA | 2007 | Human ASIC3 Genbank Accession No. NM_004769 |
| 17 | pnt | RNA | 21 | The target sequence on mouse ASIC3 mRNA for miRNA844 (510-531 relative to start site of mouse ASIC3) |
| 18 | pnt | RNA | 21 | The target sequence on mouse ASIC3mRNA for miRNA847 (259-279 relative to start site of mouse ASIC3) |
| 19 | pnt | RNA | 21 | The target sequence for human miRNA 847 (256-276 relative to start site of human ASIC3) |
| 20 | pnt | RNA | 22 | The target sequence for human miRNA 844 (507-528 relative to start site of human ASIC3) |
| 21 | pnt | DNA | 22 | the DNA sequence of the active moiety of miRNA 844 |
| 22 | pnt | DNA | 64 | Synthetic oligonucleotide for cloning miRNA845-top strand |
| 23 | pnt | DNA | 63 | Synthetic oligonucleotide for cloning miRNA845-bottom strand |
| 24 | pnt | DNA | 21 | the target sequence on mouse ASIC2 miRNA for miRNA845(404-424 relative to start site of mouse ASIC3) |
| 25 | pnt | DNA | 64 | Synthetic oligonucleotide for cloning miRNA846-top strand |
| 26 | pnt | DNA | 64 | Synthetic oligonucleotide for cloning miRNA846-bottom strand |
| 27 | pnt | DNA | 21 | the target sequence on mouse ASIC2 miRNA for miRNA846(69-89 relative to start site of mouse ASIC3) |

DETAILED DESCRIPTION

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

This invention can be better understood by reference to the following non-limiting examples. It will be appreciated by those skilled in the art that other embodiments of the invention may be practiced without departing from the spirit and the scope of the invention as herein disclosed and claimed.

1. Definitions

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

"Animal" as used herein may mean fish, amphibians, reptiles, birds, and mammals, such as mice, rats, rabbits, goats, cats, dogs, cows, apes and humans.

"Substantially complementary" used herein may mean that a first sequence is at least 60%, 65%, 70%, 75%, 80%, 85%, 90%, 95%, 97%, 98% or 99% identical to the complement of a second sequence over a region of 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

An "effective amount" refers to an amount of the RNAi agent that is capable of producing a desirable result, e.g., decreasing ASIC3 expression or activity in vitro, in vivo or ex vivo. The treatment method can be performed, alone or in conjunction with other drugs or therapy.

The term "RNAi" or "RNA interference" refers to a sequence-specific or selective process by which a target molecule (e.g., a target gene, protein or RNA) is down-regulated. Within the scope of this invention is utilization of RNAi featuring degradation of RNA molecules (e.g., within a cell). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "RNAi agent" refers to an RNA (or analog thereof) or DNA, having sufficient sequence complementarity to a target RNA (i.e., the RNA being degraded) to direct RNAi. A RNAi agent having a "sequence sufficiently complementary to a target RNA sequence to direct RNAi" means that the RNAi agent has a sequence sufficient to trigger the destruction of the target RNA by the RNAi machinery (e.g., the RISC complex) or process. An RNAi agent having a "sequence sufficiently complementary to a target RNA sequence to direct RNAi" also means that the RNAi agent has a sequence sufficient to trigger the translational inhibition of the target RNA by the RNAi machinery or process. An RNAi agent can also have a sequence sufficiently complementary to a target RNA encoded by the target DNA sequence such that the target DNA sequence is chromatically silenced. In other words, the RNAi agent has a sequence sufficient to induce transcriptional gene silencing, e.g., to down-modulate gene expression at or near the target DNA sequence, e.g., by inducing chromatin structural changes at or near the target DNA sequence. The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

miRNA (micro-RNA) is a form of single-stranded RNA which is typically 20-25 nucleotides long, and is thought to regulate the expression of other genes or a DNA polynucleotide from which the miRNA is transcribed or complementary thereto. miRNAs are RNA gene products which are transcribed from DNA, but are not translated into protein. The DNA sequence that codes for an miRNA gene is longer than the miRNA. This DNA sequence includes the miRNA encoding sequence and an approximate reverse complement. When this DNA sequence is transcribed into a single-stranded RNA molecule, the miRNA sequence and its reverse-complement base pair to form a double stranded RNA hairpin loop; this forms a primary miRNA structure (pri-miRNA) followed by its maturation into miRNAs. The function of miRNAs appears to be in gene regulation by inhibiting protein synthesis.

As used herein, taking into consideration the substitution of uracil for thymine when comparing RNA and DNA sequences, the term "substantially identical" as applied to dsRNA means that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95%, 96%, 97%, 98% or 99% identical or absolutely identical to 20 or more contiguous nucleotides of the target gene. 20 or more nucleotides means a portion, being at least about 20, 21, 22, 23, 24, 25, 50, 100, 200, 300, 400, 500, 1000, 1500, consecutive bases or up to the full length of the target gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other.

Also as used herein, the terms "nucleic acid" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the terms "contacting" and "administering" are used interchangeably, and refer to a process by which RNAi agent of the present invention is delivered to a cell, in order to inhibit expression of an ASIC3 target gene in a cell. The RNAi agent may be administered in a number of ways, including, but not limited to, direct introduction into a cell (i.e., intracellularly). Other routes of administration are described elsewhere herein.

The present invention provides novel therapeutic agents for the treatment of a variety of diseases, disorders, and conditions in which ASIC3, and/or cells that produce ASIC3, play a role. In particular, the invention provides novel therapeutics for diseases, disorders, and conditions associated with or mediated by ASIC3-expression or activity e.g., hyperalgesia and the amelioration of their manifestations (e.g., symptomatic relief of pain). The therapeutic agents are based on RNAi, a phenomenon in which double-stranded RNA containing a portion that is complementary to a target RNA leads to inhibition of the target RNA when present in a cell. The mechanism of RNAi generally involves cleavage of the target RNA or inhibition of its translation. The RNAi agents of the invention inhibit expression of cellular transcripts and thus prevent synthesis of proteins that contribute directly or indirectly to diseases, disorders, and conditions associated with or mediated by ASIC3-expression or activity. Inhibition of the ASIC3 gene expression using RNAi represents a fundamentally new therapeutic approach.

One aspect of the invention is the recognition that inhibiting expression of ASIC3 gene preferably at the level of RNA transcription, will be of significant benefit. As shown herein, RNAi agents of the present invention effectively prevent the development of primary and secondary hyperalgesia after carrageenan-induced muscle inflammation in vivo in mice injected with HSV containing the RNAi agent. See FIG. 7. The inventors have further discovered that the RNAi agents that selectively target ASIC3, when administered in vivo, unexpectedly reduce in pain-behavior similar to that as if both ASIC1 and ASIC3 were pharmacologically blocked. See Example 14 and FIG. 7.

Novel RNAi agents based on the sequences of ASIC3 as a target gene is provided herein. The invention provides RNAi agents targeted specifically to ASIC3. In various embodiments, the invention provides compositions containing microRNA (miRNA), short interfering RNA (siRNA) and/or short hairpin RNA (shRNA) targeted to ASIC3.

Figure 8:
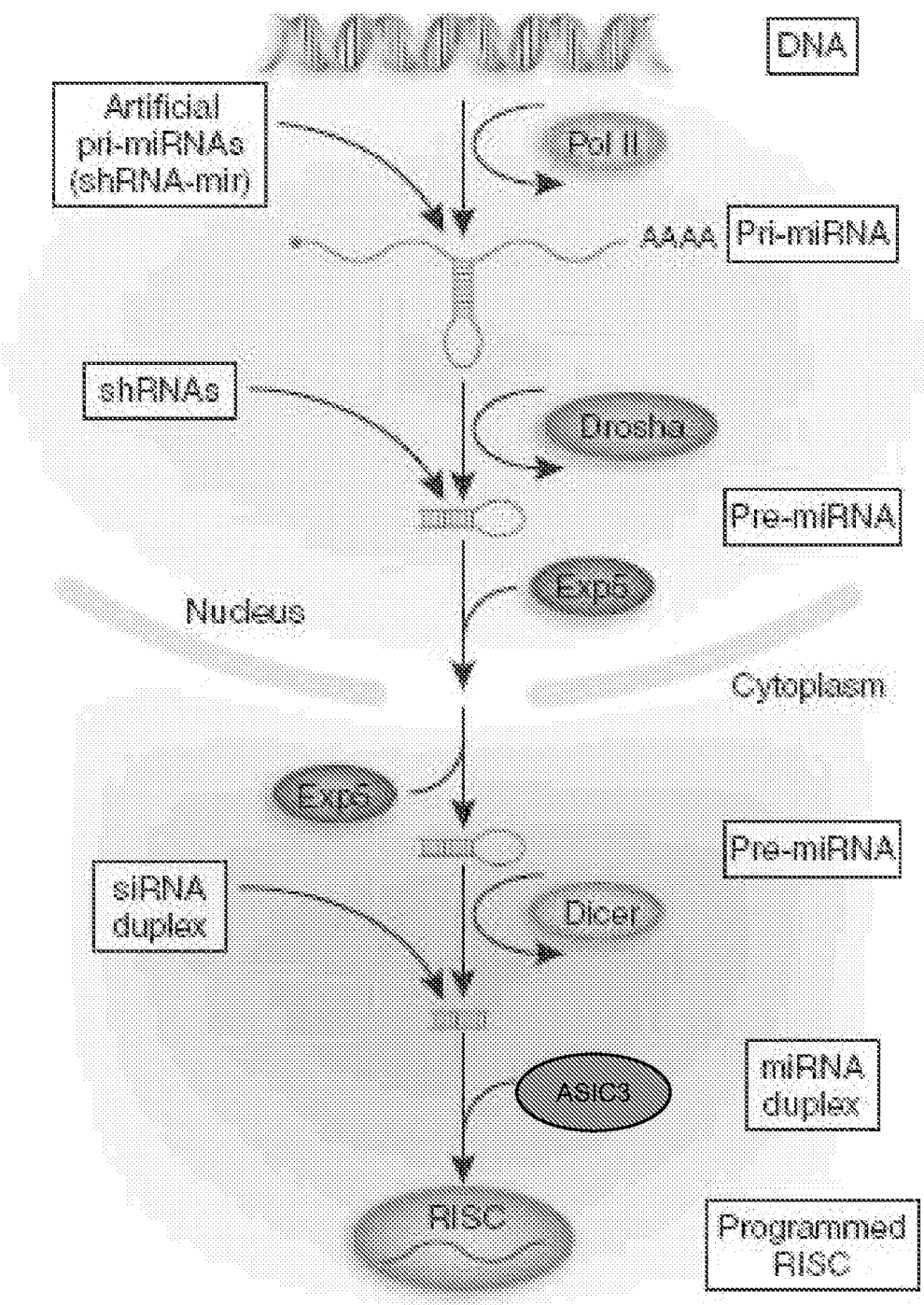
FIG. 8 shows a schematic diagram of shRNA or miRNA activity in cells.
Figure 10:
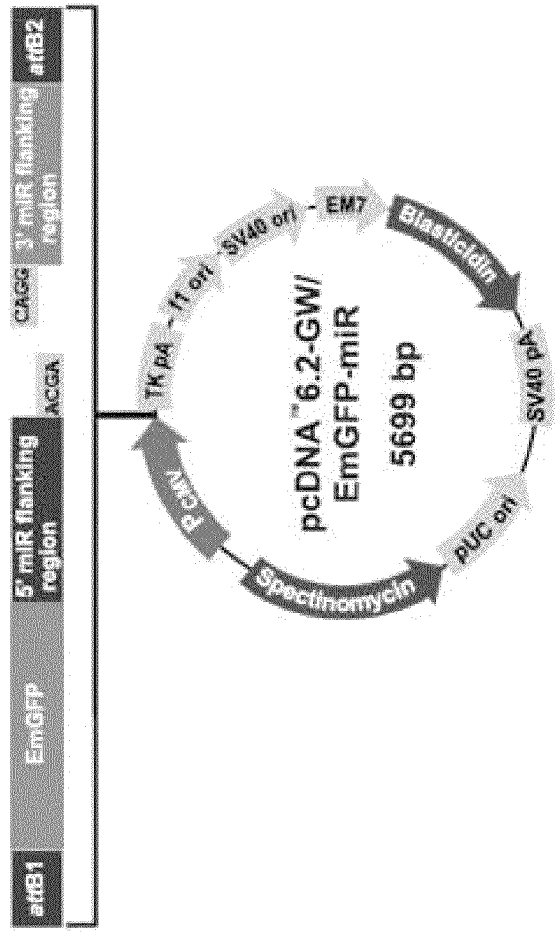
FIG. 10 shows how the two annealed synthetic oligonucleotides, shown in FIG. 9, would be ligated into the vector, pcDNA6.2-GW/EmGFP-miR.
Figure 11:
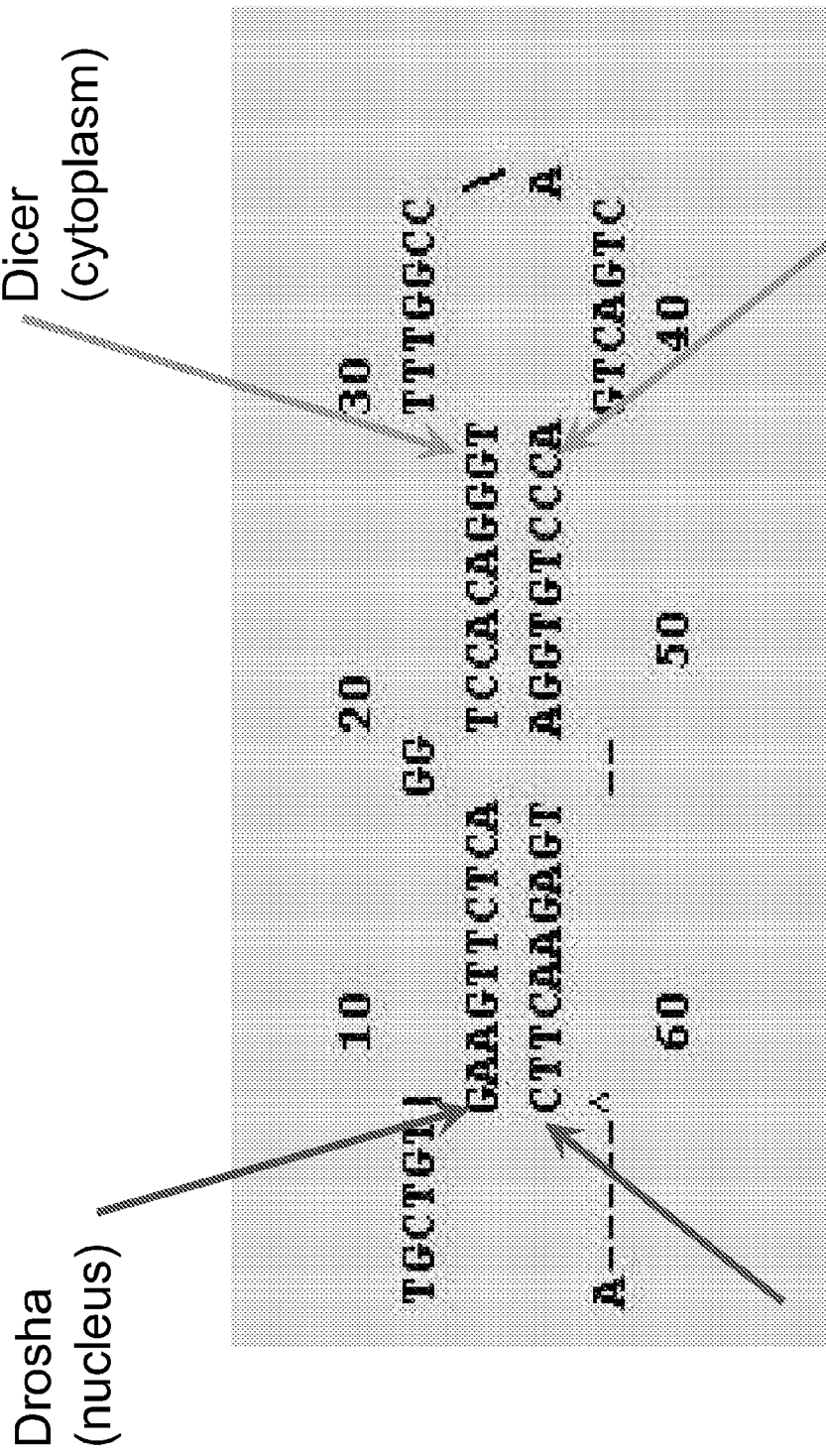
FIG. 11 shows the hairpin miRNA structure of #844, which would be generated in cells transfected with the recombinant plasmid diagrammed in FIG. 10. At the bottom of the figure, the 21 mer, GAAGTTCTCAGGTCCACAGGG, is the active moiety of miRNA844. The active moiety of miRNA844 would be made in the cytoplasm of cells, after the hairpin structure travels out of the nucleus.
Figure 12:
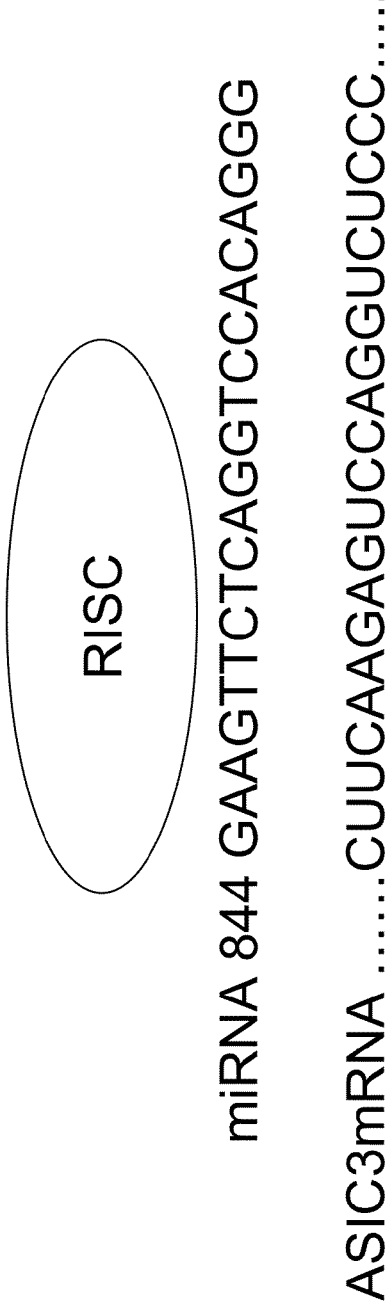
FIG. 12 shows the active moiety of miRNA844, the resultant 21 mer, annealed to the target sequence on mouse ASIC3 mRNA.

While not being bound by theory, the current model for the maturation of mammalian miRNAs is shown in FIG. 8. A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and about 2 nucleotide 3' overhang. Approximately one helical turn of the stem (about 10 nucleotides) extending beyond the Drosha cleavage site may facilitate efficient processing. The pre-miRNA may then be actively transported from the nucleus to the cytoplasm by Ran-GTP and the export receptor Ex-portin-5 (Exp5).

The pre-miRNA may be recognized by Dicer, which is also an RNase III endonuclease. Dicer may recognize the double-stranded stem of the pre-miRNA and the 5' phosphate and 3' overhang at the base of the stem loop. The terminal loop two helical turns away from the base of the stem loop may be cleaved off by Dicer leaving an additional 5' phosphate and .about.2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in miRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acid

Nucleic acids are provided herein. The nucleic acid may comprise the sequence of SEQ ID NOS: 1-27, the complement thereof, the complement of a target gene binding site, for example those referred to in Table 2 of FIG. 15, or variants thereof. The variant may be a complement of the referenced nucleotide sequence. The variant may also be a nucleotide sequence that is substantially identical to the referenced nucleotide sequence or the complement thereof. The variant may also be a nucleotide sequence that hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a polynucleotide. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

a. Pri-miRNA

The nucleic acid may comprise a sequence of a pri-miRNA or a variant thereof. The pri-miRNA sequence may comprise from 45-250, 55-200, 70-150 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-27, the complement thereof, the complement of a target gene binding site, for example those referred to in Table 2 of FIG. 15, or Example 16 table 3 or variants thereof.

The pri-miRNA may form a hairpin structure. The hairpin may comprise a first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

b. Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein, The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-27, the complement thereof, the complement of a target gene binding site, for example those referred to in Table 2 of FIG. 15, or variants thereof.

c. miRNA

The nucleic acid may also comprise a sequence of a miRNA (including miRNA*) or a variant thereof. The miRNA sequence may comprise from 13-33, 18-24 or 21-23 or more nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be any suitable nucleotides of the pre-miRNA. In some examples, the sequence of the miRNA may be the first 13-33 nucleotides of the pre-miRNA. In some examples, the sequence of the miRNA may also be the last 13-33 nucleotides of the pre-miRNA. The sequence of the miRNA may comprise the sequence of SEQ ID NOS: 1-21, the complement thereof, the complement of a target gene binding site, for example those referred to in Table 2 of FIG. 15, or variants thereof.

d. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially complementary to the 5' of a miRNA and at least 5-12 nucleotides that are substantially identical to the flanking regions of the target site from the 5' end of the miRNA, for the purposes of binding to a miRNA and repressing its activity; or (b) at least 5-12 nucleotides that are substantially identical to the 3' of a miRNA and at least 5 nucleotide that are substantially complementary to the flanking region of the target site from the 3' end of the miRNA, for the purposes of inhibiting the ability of a miRNA to bind to its target. The sequence of the anti-miRNA may comprise SEQ ID NOS: 1-27, the complement of SEQ ID NOS: 1-27, the complement of a target gene binding site referred to in Table 2, or variants thereof.

e. Binding Site of Target

The nucleic acid may also comprise a sequence of a target miRNA binding site, or a variant thereof. The target site sequence may comprise a total of 5-100, preferably 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 contiguous polynucleotides of the sequence of ASIC3, for example, the mRNA of ASIC3. The DNA is identified in SEQ ID NOS:15-

16 (see also NM_183000 (mouse) and NM_004769 (human), or a target gene binding site referred to in Table 2 (FIG. 15), for example, 510-531 or 259-279 relative to the start of the coding sequence of Genbank Accession No. NM_183000 (mouse) (SEQ ID NO:15) and 507-528 or 256-276 relative to the start of the coding sequence of Genbank Accession No. NM_004769 (human)(SEQ ID NO:16).] See, for example, SEQ ID NOS:5, 17-20.

In certain embodiments of the invention the miRNA comprises two RNA strands having a region of complementarity approximately 60 nucleotides in length, but ranging in length between 10, 20, 30, 40, 50, 60 or more nucleotides, and optionally further comprises 1, 2, 3, 4 or more single-stranded overhangs.

In certain embodiments of the invention when the RNAi agent is shRNA, the shRNA comprises a single RNA molecule having a region of self-complementarity. The single RNA strand forms a hairpin structure comprising a stem and loop and, optionally, one or more unpaired portions at the 5' and/or 3' end of the RNA. Such RNA species are said to self-hybridize.

In addition, the invention provides vectors whose presence within a cell results in transcription of one or more RNAs that self-hybridize or hybridize to each other to form a miRNA, an shRNA or siRNA that inhibits expression of at least one target transcript that encodes ASIC3.

The invention further provides compositions, e.g., pharmaceutical compositions, comprising the inventive RNAi agents (miRNAs, siRNAs, shRNAs, and/or vectors, and methods of delivery of such compositions. For example, the invention provides a vector comprising a nucleic acid operably linked to expression signals (e.g., a promoter or promoter/enhancer) active in a cell so that, when the construct is introduced into the cell, a miRNA, an siRNA or shRNA is produced inside the host cell that is targeted to the ASIC3 transcript. In general, the vector may be a DNA or RNA plasmid or a virus vector such as a retrovirus (e.g., a lentivirus), adenovirus, adeno-associated virus, herpes virus, vaccinia virus, etc. whose presence within a cell results in transcription of one or more ribonucleic acids (RNAs) that self-hybridize or hybridize to each other to form a short hairpin RNA (shRNA) or short interfering RNA (siRNA) that inhibits expression of at least one target transcript in the cell, which transcript is involved either directly or indirectly in mast cell or basophil activity and/or in the production of ASIC3 by B cells. In certain embodiments of the invention the vector comprises a nucleic acid segment operably linked to a promoter, so that transcription results in synthesis of an RNA comprising complementary regions that hybridize to form an shRNA targeted to the target transcript. In certain embodiments of the invention the vector comprises a nucleic acid segment flanked by two promoters in opposite orientation, wherein the promoters are operably linked to the nucleic acid segment, so that transcription from the promoters results in synthesis of two complementary RNAs that hybridize with each other to form an siRNA targeted to the target transcript. The invention further provides compositions comprising the vector.

Any of the inventive compositions may comprise, in addition to the siRNAs, shRNAs, and/or vectors described herein, one or more substances, referred to as delivery agents, that facilitate delivery and/or uptake of the miRNA, siRNA, shRNA, or vector. These substances include cationic polymers; peptide molecular transporters including arginine-rich peptoids or peptides and histidine-rich peptides; cationic and neutral lipids; liposomes; certain non-cationic polymers; carbohydrates; and surfactant materials. Suitable delivery agents are described in co-pending U.S. patent application Ser. No. 10/674,159 (published as US2004242518) and U.S. Ser. No. 10/674,087, published as US2005008617) and PCT applications published as WO2004028471 and WO2004029213, all of which are incorporated herein by reference. The compositions may be administered by a variety of routes and are described elsewhere herein.

Reducing Expression of a ASIC3 Gene

A method of reducing expression of a target gene, ASIC3, in a cell, tissue or organ is also provided. Expression of the ASIC3 gene may be reduced by expressing a nucleic acid described herein that comprises a sequence substantially complementary to one or more binding sites of the target ASIC3 mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target ASIC3 mRNA, which may lead to activation of RISC-mediated gene silencing. An example for a study employing over-expression of miRNA is Yekta et al 2004, Science 304-594, which is incorporated herein by reference. One of ordinary skill in the art will recognize that the nucleic acids described herein may also be used to inhibit expression of an ASIC3gene or inhibit activity of miRNAs using antisense methods well known in the art, as well as RNAi methods described in U.S. Pat. Nos. 6,506,559 and 6,573,099, which are incorporated by reference. Examples for efficient suppression of miRNA expression are the studies by Esau et al 2004 JBC 275-52361; and Cheng et al 2005 Nucleic Acids Res. 33-1290, which is incorporated herein by reference.

The ASIC3 RNAi agent can be tested for its ability to repress gene expression or channel activity of ASIC3 in vitro, e.g. CHO cells or cells expressing ASIC3. See Examples 12 and 13. ASIC3 expression levels of RNA or protein and the modulation of these levels can be assayed in a variety of ways known in the art. For example, mRNA levels can be quantitated by, e.g., Northern blot analysis, competitive polymerase chain reaction (PCR), or real-time PCR (RT-PCR). RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of ASIC3 can be quantitated in a variety of ways well known in the art, such as immunoprecipitation, Western blot analysis (immunoblotting), ELISA or fluorescence-activated cell sorting (FACS). Antibodies directed to ASIC3 can be identified and obtained from a variety of sources or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997. Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

A decrease in the amount of ASIC3, for example, the mRNA or protein level of ASIC3, in the presence of the RNAi agent as compared to the mRNA or protein level of ASIC3 in the absence of the RNAi agent indicates that the RNAi agent decreases ASIC3 expression. Such agents may be suitable for treating diseases, disorders, or conditions associated with ASIC3 expression or activity, such as hyperalgesia.

Reducing Activity of an Acid Sensing Ion Channel (ASIC) having ASIC3

A method of reducing ASIC channel activity in a cell in vitro or in vivo is also provided. Activity of an ASIC channel including one or more ASIC3, e.g. acid sensing ion channels that are homologous or heterologous for ASIC3, may be reduced by expressing a nucleic acid described herein, e.g. RNAi agent. As discussed elsewhere herein the RNAi agent may have a sequence substantially complementary to one or more binding sites of the target ASIC3 mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target ASIC3 mRNA, which may lead to activation of RISC-mediated gene silencing. An example for a study employing over-expression of miRNA is Yekta et al 2004, Science 304-594, which is incorporated herein by reference.

Methods of measuring ASIC3's ion channel activity are also known in the art. Examples of the methods include using whole-cell patch recording (Waldmann et al., J Biol Chem 272, 20975-20978 (1997); Voilley et al., J Neurosci 21, 8026-8033 (2001); Molliver et al., Molecular Pain 1:35 (2005); using voltage-sensitive dye (Felix et al., Assay Drug Dev Technol. 2, 260-268 (2004); Sharma et al., Biophys J 88, 3038-3049 (2005)), using ion-sensitive dyes and cytotoxicity assay (Weiser, J Neurosci Methods 137, 79-85 (2004).

To determine the ability of the RNAi agent to inhibit an ASIC having one or more ASIC3, the activity may be compared with a control activity of the same ASIC in the absence of the RNAi agent. A "control" provides a reference point for measuring changes in phenotype of the subject cell or ASIC. A control typically comprise, for example, a cell, that is not contacted with the RNAi agent.

If the expression of ASIC3 or activity of the ASIC having at least one ASIC3 or both is lower than the control, the RNAi agent is identified as being effective for treating diseases, disorders, or conditions associated with ASIC3. One can further verify the efficacy of an RNAi agent in vivo, for example, using an animal or animal model. One can administer the RNAi agent to the animal models and evaluation the agent for efficacy using standard techniques. Any statistically significant improvement, for example, lessening pain, such as primary or secondary hyperalgesia or both, indicates the RNAi agent may be used for treating diseases, disorders or conditions associated with ASIC3 activity or expression.

Increasing Expression of a Target ASIC3 Gene

A method of increasing expression of a target ASIC3 gene in a cell, tissue or organ is also provided. Expression of the target gene may be increased by expressing a nucleic acid described herein that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid that is substantially complementary to a portion of the binding site in the target gene, such that binding of the nucleic acid to the binding site may prevent miRNA binding. Methods for determining ASIC3 mRNA or protein levels are described elsewhere herein and are known to one skilled in the art, Increasing Activity of an Acid Sensing Ion Channel (ASIC) having ASIC3

A method of increasing ASIC channel activity in a cell in vitro or in vivo is also provided. Activity of an ASIC channel including one or more ASIC3, e.g. acid sensing ion channels that are homologous or heterologous for ASIC3, may be increased by expressing a nucleic acid described herein, e.g. a polynucleotide encoding ASIC3 or a polynucleotide complementary to the RNAi agent. Techniques for determining the activity are described elsewhere herein and are also known to one skilled in the art.

An increase in the amount of ASIC3, for example, the mRNA or protein level of ASIC3, in the presence of a polynucleotide complementary to the RNAi agent as compared to the mRNA or protein level of ASIC3 in the absence of the polynucleotide complementary to the RNAi agent indicates that the polynucleotide increases ASIC3 expression. Such compounds may be suitable for treating diseases, disorders, or conditions associated with ASIC3 under-expression or activity.

Designing or Selecting ASIC3 RNAi Agents

The present invention also provides methods for identifying RNAi agents having sequences that are useful for the treatment or prevention of diseases, disorders, or conditions associated with ASIC3 expression or activity or associated with a decrease in extracellular pH. Exemplary diseases, disorders, or conditions are described elsewhere. Additional potential RNAi agents that target ASIC, e.g. human and mouse ASIC3 mRNA, may be identified using any suitable technique, for example, using software that predicts potential miRNA for a given target. See, for example, BLOCK-iT™ RNAi designer software from Invitrogen, Carlsbad, Calif. In some examples, RNAi agents include those that are based on, comprise or consist of one of the these sequences provided herein, for example, those identified in Tables 1 and 2 which provides exemplary RNAi agents targeting ASIC3. Accordingly, additional RNAi agents may include at least a portion of the sequence included in the RNAi agents.

Some exemplary RNAi agents, miRNA844, miRNA847, miRNA Hu844, and miRNA Hu847, shown herein are composed of a sense strand and an antisense strand of 22, 21, 22, and 21 nucleotides in length. However, while these lengths may potentially be optimal, the RNAi agents are not meant to be limited to these lengths. The skilled person is well aware that shorter or longer RNAi agents may be similarly effective, since, within certain length ranges, the efficacy is rather a function of the nucleotide sequence than strand length. For example, Yang, D., et al., PNAS 2002, 99:9942-9947, demonstrated similar efficacies for RNAi agents of lengths between 21 and 30 base pairs. Others have shown effective silencing of genes by RNAi agents down to a length of approx. 15 base pairs (Byrom, W. M., et al., Inducing RNAi with sRNAi Cocktails Generated by RNase III; Tech Notes 10(1), Ambion, Inc., Austin, Tex., USA).

Therefore, it is possible and contemplated by the instant invention to select from the sequences provided herein and described in Tables 1 and 2 a partial sequence of between 15 to 22 nucleotides for the generation of an RNAi agent, miRNA, derived from one of the sequences described in Tables 1 and 2. Alternatively, one may add one or several nucleotides to one of the sequences provided in Tables 1 and 2, preferably, but not necessarily, in such a fashion that the added nucleotides are complementary to the respective sequence of the target gene, e.g. ASIC3. All such derived RNAi agents are included in the RNAi agents of the present invention, provided they essentially retain the ability to inhibit ASIC3 expression or activity in vitro or in vivo.

Generally, the RNAi agents of the instant invention include a region of sufficient complementarity to the ASIC3 gene, and are of sufficient length in terms of nucleotides, that the RNAi agent, or a fragment thereof, can mediate down regulation of the ASIC3 gene. The antisense strands of the RNAi agents may be fully complementary to the target ASIC3 mRNA sequences, e.g. mouse or human ASIC3, and their sense strands may be fully complementary to the antisense strands. However, it is not necessary that there be perfect complementarity between the RNAi agent and the target, but the correspondence must be sufficient to enable the RNAi agent, or a cleavage product thereof, to direct sequence specific silencing, e.g., by RNAi cleavage of an ASIC3 mRNA.

Therefore, the RNAi agents of the instant invention include agents that target ASIC3. In some example, the RNAi agents comprise a sense strand and antisense strand each comprising a sequence of at least 14, 15, 16, 17, 18, 19, 20, 21, 22 or more nucleotides which is essentially identical, as defined below, to one of the sequences described in Tables 1 and 2, except that not more than 1, 2 or 3 nucleotides per strand, respectively, have been substituted by other nucleotides (e.g. adenosine replaced by uracil), while essentially retaining the ability to inhibit ASIC3 in vitro or in vivo. In some examples, the RNAi agents will therefore possess at least 14, 15, 16, 17, 18, 19, 20, 21, 22 or more nucleotides identical to one of the sequences of in vitro or in vivo, but 1, 2 or 3 base mismatches with respect to either the target ASIC3 mRNA sequence or between the sense and antisense strand are introduced. Mismatches to the target ASIC3 mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

The antisense strand of an RNAi agent should be equal to or at least, 14, 15, 16 17, 18, 19, 25, 29, 40, or 50 nucleotides in length. It should be equal to or less than 60, 50, 40, or 30, nucleotides in length. Preferred ranges are 15-30, 17 to 25, 19 to 23, and 19 to 21 nucleotides in length.

The sense strand of an RNAi agent should be equal to or at least 14, 15, 16 17, 18, 19, 25, 29, 40, or 50 nucleotides in length. It should be equal to or less than 60, 50, 40, or 30 nucleotides in length. Preferred ranges are 15-30, 17 to 25, 19 to 23, and 19 to 21 nucleotides in length.

The double stranded portion of an RNAi agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotides pairs in length. Preferred ranges are 15-30, 17 to 25, 19 to 23, and 19 to 21 nucleotides pairs in length.

It is preferred that the sense and antisense strands be chosen such that the RNAi agent includes a single strand or unpaired region at one or both ends of the molecule. Thus, an RNAi agent contains sense and antisense strands, preferably paired to contain an overhang, e.g., one or two 5' or 3' overhangs but preferably a 3' overhang of 2-3 nucleotides. Most embodiments will have a 3' overhang. Preferred sRNAi agents will have single-stranded overhangs, preferably 3' overhangs, of 1 to 4, or preferably 2 or 3 nucleotides, in length at each end. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the mRNAi agent range discussed above. mRNAi agents can resemble in length and structure the natural Dicer processed products from long dsRNAs. Embodiments in which the two strands of the mRNAi agent are linked, e.g., covalently linked are also included. Hairpin, or other single strand structures which provide the required double stranded region, and preferably a 3' overhang are also within the invention.

In many embodiments of the invention a ds RNAi agent, e.g., a partially ds RNAi agent, is required or preferred. Thus, it is understood that that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

The RNAi agents, miRNAs, siRNAs and/or shRNAs, may be obtained using any suitable method or technique, for example, by chemical synthesis, in vitro transcription, in vivo intracellular transcription, etc. A method of synthesizing the reverse-complement of an ASIC3 target nucleic acid is also provided. The reverse complement may be synthesized according to methods outlined in U.S. patent Ser. No. 11/384, 049, the contents of which are incorporated herein by reference in its entirety.

The RNAi agent may be expressed from an expression vectors, and the nucleic acid sequence encoding an ASIC3 RNAi agent operatively linked to a promoter or enhancer-promoter combination that allows for expression in a desired cell. Suitable expression vectors include plasmids and viral vectors such as herpes viruses, retroviruses, vaccinia viruses, attenuated vaccinia viruses, canary pox viruses, adenoviruses and adeno-associated viruses. In some examples, the virus is replication defective.

Evaluation of Candidate RNAi Agents

A candidate RNAi agent can be evaluated for its ability to downregulate target ASIC3 gene expression. For example, a candidate RNAi agent can be provided, and contacted with a cell, e.g. a cell expressing ASIC3, that expresses the target gene, e.g., the ASIC3 gene, either endogenously or because it has been transfected with a construct from which ASIC3 can be expressed. The level of target gene expression prior to and following contact with the candidate RNAi agent can be compared, e.g. on an mRNA or protein level. If it is determined that the amount of RNA or protein expressed from the target gene is lower following contact with the RNAi agent, then it can be concluded that the RNAi agent downregulates target gene expression. The level of target ASIC3 RNA or ASIC3 protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis. Other techniques are described herein and will be known to one skilled in the art.

Stability Testing, Modification, and Retesting of RNAi Agents

A candidate RNAi agent can be evaluated with respect to stability, e.g., its susceptibility to cleavage by an endonuclease or exonuclease, such as when the RNAi agent is introduced into the body of a subject, e.g. animal. Methods can be employed to identify sites that are susceptible to modification, particularly cleavage, e.g., cleavage by a component found in the body of a subject.

When sites susceptible to cleavage are identified, a further RNAi agent can be designed and/or synthesized wherein the potential cleavage site is made resistant to cleavage, e.g. by introduction of a 2'-modification on the site of cleavage, e.g. a 2'-O-mathyl group. This further RNAi agent can be retested for stability, and this process may be iterated until an RNAi agent is found exhibiting the desired stability.

In Vivo Testing

An RNAi agent identified as being capable of inhibiting ASIC3 gene expression can be tested for functionality in vivo in an animal model (e.g., in a mammal, such as in mouse or rat). For example, the RNAi agent can be administered to an animal, and the RNAi agent evaluated with respect to its biodistribution, stability, and its ability to inhibit ASIC3 gene expression. The RNAi agent can be administered directly to the target tissue, such as by injection. Other modes and routes of administration will be well known to one skilled in the art and are also described elsewhere herein.

Treating Diseases, Disorders, or Conditions Associated with ASIC3

The present invention further provides methods of treating or preventing diseases, disorders, or conditions associated with ASIC3 expression or activity or associated with a decrease in extracellular pH. The diseases, disorders, and conditions include but are not limited to pain conditions, particularly primary and/or secondary hyperalgesia, musculoskeletal pain, inflammation, ischemia, arthritis, anxiety, fibromyalgia, chronic fatigue syndrome, sepsis, muscular dystrophy, depression, fear, stroke, cancer, stress, post-traumatic stress disorder, diabetes, insulin resistance, multiple sclerosis and the like. In some examples, symptomatic relief may be provided by administering compositions containing one or more RNAi agents of the present invention to a subject at risk of or suffering from at least one of these diseases, disorders, and conditions within an appropriate time window prior to, during, or after exposure to a triggering stimulus such as a deep tissue injury.

The efficacy of the ASIC3 RNAi agent in treating or preventing a particular disease, disorder, or condition can be evaluated both in vitro and in vivo. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to hyperalgesia, treatment may be measured quantitatively or qualitatively to determine the presence/absence of the disease, or its progression or regression using, for example, reduction in muscle inflammation and mechanical sensitivity and/or no worsening in disease over a specified period of time or other symptoms associated with the disease or clinical indications associated with the pathology of hyperalgesia. For in vivo studies, the ASIC3 RNAi agent can be injected into an animal (e.g., an animal model) and its effects on a disease, disorder, or condition or symptom of a disease, disorder, or condition evaluated. See, for example, Example 14 herein.

Based on the results of the in vivo experiments, an appropriate dosage range and administration route for in vivo administration can be determined. The dosage required depends on the choice of the route of administration; the nature of the formulation; the nature of the patient's illness; the subject's size, weight, surface area, age, and sex; other drugs being administered; and the judgment of the attending physician. As is well known in the art, the dosage for a patient depends upon various factors as described above. Dosages will vary, but a preferred dosage for administration of polynucleotide is about $10^6$ to $10^{12}$ copies of the RNAi agent, such as a polynucleotide molecule. This dose can be administered as needed. Any suitable route of administration may be used to deliver the RNAi agent or composition comprising the RNAi agent of the present invention.

Compositions

As mentioned above, the compositions of the present invention may be used in the treatment and/or prophylaxis of any of a variety of diseases, disorders, or conditions in which involvement of ASIC3 is implicated, including hyperalgesia, etc. In addition, they may be used for a variety of other purposes in which it is desired to inhibit expression of the target ASIC3 gene, e.g., for research purposes such as to study the genes themselves, to test candidate pharmaceutical agents, etc.

In one aspect, a composition for use in the methods described herein include a polynucleotide containing a nucleic acid sequence of an RNAi agent or encoding an ASIC3 RNAi agent of the present invention, for example, an anti-sense RNA, a small interfering RNA (siRNA), miRNA, a shRNA, a dsRNA, and the like that targets ASIC3 and inhibits ASIC3 expression or channel activity. A pharmaceutical composition is also provided. Accordingly, the pharmaceutical composition may comprise a nucleic acid of any of the RNAi agents described herein and optionally a pharmaceutically acceptable carrier. The pharmaceutical composition may be administered by any suitable known methods or technique. Commonly used gene transfer techniques include calcium phosphate, DEAE-dextran, electroporation, microinjection, viral methods and cationic liposomes and vectors.

In an in vivo approach, an RNAi agent that targets ASIC3 is administered to a subject. Generally, the RNAi agent is in a pharmaceutically-acceptable carrier (e.g., physiological saline). A composition of the present invention, such as a pharmaceutical composition, may comprise different types of acceptable carriers depending on whether it is to be administered in solid, liquid or aerosol form, and whether it needs to be sterile for such routes of administration as injection. The compositions comprising one or more RNAi agents may be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference). A number of suitable formulations for use in the present invention are found in Remington's Pharmaceutical Sciences (Mack Publishing Company, Philadelphia, Pa., 17th ed., 1985) and in Dermatological Formulations: Percutaneous absorption, Barry (Ed.), Marcel Dekker Inc., 1983, both incorporated herein by reference. Moreover, for a brief review of methods for drug delivery, see Langer, Science 249:1527-1533, 1990, which is also incorporated herein by reference.

The composition can be any dose or effective amount of the composition that is safe and efficacious to achieve the desired result. As the diseases, disorders or conditions that would benefit from these compositions are well known, the compositions may be designed such that they contain appropriate levels effective for treatment of the particular disease, disorder or condition. The compositions may generally be used in any formulation that is effective for treatment and the intended mode of administration.

The comprising the RNAi agent polynucleotide can be delivered by the use of polymeric, biodegradable microparticle or microcapsule delivery devices known in the art. Another way to achieve uptake of the nucleic acid is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The ASIC3 RNAi agent can be formulated into dosage forms for different administration routes utilizing conventional methods. For example, the RNAi can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the ASIC3 RNAi agent with a solid carrier and a lubricant. Examples of solid carriers include starch and sugar bentonite. The ASIC3 RNAi agent can also be administered in a form of a hard shell tablet or a capsule containing a binder, e.g., lactose or mannitol, a conventional filler, and a tableting agent. The ASIC3 RNAi agent can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The compositions of the invention can be administered to any part of the body that renders the composition safe and effective for treatment of a particular disease, disorder or condition. It will be appreciated that the present methods of treatment can be applied alone or in combination with treatments for these diseases, disorders or conditions. The compositions useful in the present methods can be administered one time or multiple times, depending on the composition, the severity of the disease, disorder, or condition, and the initial response of the condition to the treatment, for example, alleviating a symptom. For example, the compositions can be administered 1, 2, 4, or more times per day, and can be administered every 1, 2, 4, 7, or more days. Such treatments can be administered for a limited duration, or indefinitely until the condition or symptom has resolved. The compositions can be administered locally or systemically. In certain preferred embodiments of the invention the compositions comprise one or more RNAi agents, such as miRNAs, siRNAs and/or shRNAs For treatment of deep tissue, the RNAI agent can be delivered directly to the tissues or surrounding tissues via injection.

```
SEQUENCES:
Synthetic Oligonucleotides for Cloning Mouse ASIC3
miRNA844
Mmi513844 top strand
                                         (SEQ ID NO: 1)
TGCTGTGAAGTTCTCAGGTCCACAGGGTTTTGGCCACTGACTGACCCTG

TGGATGAGAACTTCA

Synthetic Oligonucleotides for Cloning Mouse ASIC3
miRNA844
Mmi513844 bottom strand
                                         (SEQ ID NO: 2)
CCTGTGAAGTTCTCATCCACAGGGTCAGTCAGTGGCCAAAACCCTGTG

GACCTGAGAACTTCAC

Synthetic Oligonucleotides for Cloning Mouse ASIC3
miRNA844 annealed
(Sequences 1 and 2 annealed).
The active moiety of the miRNA844 sequence is
underlined)
                                         (SEQ ID NO 3)
TGCTGT GAAGTTCTCAGGTCCACAGGGT TTTGGCCACTGACTGACC

CTGTGGATGAGAACTTCACA CTTCAAGAGTCCAGGTGTCCCA AAAC

CGGTGACTGACTGGGACACCTACTCTTGAAGTGTCC

The DNA sequence of the active moiety of miRNA 844
                                         (SEQ ID NO: 4)
GAAGTTCTCAGGTCCACAGGGT The target sequence of miRNA844 on ASIC3 mRNA
                                         (SEQ ID NO: 5)
CUUCAAGAGUCCAGGTCTCCC Synthetic Oligonucleotides for Cloning Mouse ASIC3
miRNA847
Mmi 513847 top strand
                                         (SEQ ID NO: 6)
TGCTGTACACAAAGTGACAGCTGGGAGTTTTGGCCACTGACTGACTCC

CAGCTCACTTTGTGTA

Synthetic Oligonucleotides for Cloning Mouse ASIC3
miRNA847
Mmi 513847 bottom strand
                                         (SEQ ID NO: 7)
CCTGTACACAAAGTGAGCTGGGAGTCAGTCAGTGGCCAAAACTCCCAG

CTGTCACTTTGTGTAC

The DNA sequence of the active moiety of miRNA847
                                         (SEQ ID NO: 8)
TACACAAAGTGACAGCTGGGA Synthetic Oligonucleotides for Cloning Human ASIC3
miRNA844
Hsa844 analog top strand
                                         (SEQ ID NO: 9)
TGCTGTGAAGTTCTCAGGCCCACAAGGTTTTGGCCACTGACTGACCTT

GTGGGTGAGAACTTCA
```

Synthetic Oligonucleotides for Cloning Human ASIC3 miRNA844
Hsa844 analog bottom strand
(SEQ ID NO: 10)
CCTGTGAAGTTCTCACCCACAAGGTCAGTCAGTGGCCAAAACCTTGTG

GGCCTGAGAACTTCAC

The DNA sequence of the active moiety of miRNA Hu844
(SEQ ID NO: 11)
TGAAGTTCTCAGGCCCACAAGG Synthetic Oligonucleotides for Cloning Human ASIC3 miRNA847
Hsa847 analog top strand
(SEQ ID NO: 12)
TGCTGTGCACAGGGTGACAGCCGGGAGTTTTGGCCACTGACTGACTCC

CGGCTCACCCTGTGCA

Synthetic Oligonucleotides for Cloning Human ASIC3 miRNA847
Hsa847 analog bottom strand
(SEQ ID NO: 13)
CCTGTGCACAGGGTGAGCCGGGAGTCAGTCAGTGGCCAAAACTCCCGG

CTGTCACCCTGTGCAC

The DNA sequence of the active moiety of miRNA Hu847
(SEQ ID NO: 14)
TGCACAGGGTGACAGCCGGGA Mouse ASIC3 Genbank Accession No. NM_183000 (mouse) cds starts at 262 (start site underlined) and continues to 1854
(SEQ ID NO: 15)
cagagacccagccccacggagtcaacgcctgttctggggaaggcagag ctgaccgaagttcaactcatccagtcctatcaggccagtactttcacc tgtcttggctcctcccgtctctaccttctccttctctctccgtattcc ttgctgagctacttgagtcccatttcaatccccaccactatcctgcta gccctacaaaacagcttccgtgctccttagaaatcccatccccagtca ggaaacctccctgctccagcatgaaacctccctcaggactggaggag gcccagcggcgacaggcctcagacatccgggtgttcgccaacagctgc acgatgcatggtttgggccacatctttggccctggaggcctgaccctg cgccgtgggctgtgggccacagctgtactcctgtcgctggcggccttc ctctaccaggtggctgagcgggttcgctactatggggagttccaccat aagaccaccctggatgagcgtgagagccaccagcttaccttcccagct gtcactttgtgtaacatcaatcccctgcgccgctcacgcctcacaccc aatgacttgcactgggccggaacggcactgctgggtctggaccctgct gaacatgctgcctaccttcgtgccctgggccagcccctgcaccacct ggcttcatgccagtccgacttttgacatggcacaactctacgccaga gccgccactcccttgaggacatgttgctggactgccgataccgtggc cagccctgtggacctgagaacttcacagtgattttcactcgaatgggg caatgctacaccttcaactctggtgcccaggggcagagctgctcacc actcctaagggcggtgctggcaatggactggagattatgctggatgta cagcaggaggagtatctgcccatctgaaggacatggaagagacccca tttgaggtggggatccgagtgcagatccacggccaggaggaacccct gccattgaccagctgggcttcggtgctgccccaggccaccagactttt gtgtcctgccagcaacagcaactgagtttcctgccaccaccctggggt gactgcaataccgcatctgtggatcccgactttgatccagagccctct gatcccctgggttcccctagctccagccctccttatagcttaatagg tgtcgcctggcctgtgagtcacgctatgtggctcggaagtgcggatgt cgaatgatgcatatgcctggaaactcccagtgtgcagcccccagcag tacaaggactgtgccagcccagctctggacgctatgctgcgaaaggac acttgtgtctgtcccaacccgtgcgccactacacgctatgccaaggag ctctccatggtgcggattcccagccgcgcttcagctcgctacctggcc cggaaatacaaccgtagcgagacttacatcacggagaatgtactggtt ctggatatcttctttgaagccctcaactatgaggccgtggaacaaaag gcagcttatgaagtgtcggagttgctgggagacattgggggacagatg ggactgtttatcggagccagcctgcttaccatcctcgagatcctcgac tacctctgtgaggttttcaagacagagtcctggggtacttctggaac agaaggagctctcaaaggcgctctggcaacactctgctccaggaagag ttgaatgggcatcgaacacatgttccccatctcagcctaggccccagg cctcctaccgctcccagtgctgtcaccaagacactcgctgcctcccac cgtacctgttaccctcgtgacaaggctctagacctgcttggctgcgccg tgacatcttggacatgcccaggctgtacatctttgccttctttaccct aataaagctctagtacacgtgcaaaaaaaaaaaaaaaaaaaaaaaaaa aaaaaaaaa Human ASIC3 Genbank Accession No. NM_004769 (human) cds starts at 369 (start site underlined) and continues to 1964.
(SEQ ID NO: 16)
ctgaaacccaatcctctgcagcagcgccggctcagcaccgccggctca gcaccgctccgcagccctgcctgccacggtcagctacgtcccacctg gtctgctgcggagtccccagcccagtgcctagcccagtggagccaccg cctgttcctcgggaaggaacagtgggacctgaccggccagatcacctc ctccaatcctgccaggctagtgcctccctgccttccaaccttggctgt ctcccaccctctcttctcctctccttgcctggcctcctgaatcctatc ttagcctccttagcccctgactgactctctctcgcttcttccaagcc tctgtagctggttccgctcctgggttctggccatgaagcccacctcag gcccagaggaggcccggcggccagcctcggacatccgcgtgttcgcca gcaactgctcgatgcacgggctgggccacgtcttcgggccaggcagcc tgagcctgcgccgggggatgtgggcagcggccgtggtcctgtcagtgg ccaccttcctctaccaggtggctgagagggtgcgctactacaggggagt tccaccaccagactgccctggatgagcgagaaagccaccggctcatct tcccggctgtcaccctgtgcaacatcaaccactgcgccgctcgcgcc taacgcccaacgacctgcactgggctgggtctgcgctgctgggcctgg atcccgcagagcacgccgcttcctgcgcgcccctgggccggccccctg caccgcccggcttcatgccagtcccacctttgacatggcgcaactct atgcccgtgctgggcactccctggatgacatgctgctggactgtcgct -continued tccgtggccaaccttgtgggcctgagaacttcaccacgatcttcaccc ggatgggaaagtgctacacatttaactctggcgctgatggggcagagc tgctcaccactactaggggtggcatgggcaatgggctggacatcatgc tggacgtgcagcaggaggaatatctacctgtgtggagggacaatgagg agacccgtttgaggtggggatccgagtgcagatccacagccaggagg agccgcccatcatcgatcagctgggcttgggggtgtccccgggctacc agacctttgtttcttgccagcagcagcagctgagcttcctgccaccgc cctggggcgattgcagttcagcatctctgaacccaactatgagccag agccctctgatcccctaggctccccagcccagcccagccctccct ataccttatgggtgtcgcctggcctgcgaaacccgctacgtggctc ggaagtgcggctgccgaatggtgtacatgccaggcgacgtgccagtgt gcagccccagcagtacaagaactgtgcccacccggccatagatgcca tgcttcgcaaggactcgtgcgcctgccccaacccgtgcgccagcacgc gctacgccaaggagctctccatggtgcggatcccgagccgcgccgccg cgcgcttcctggcccggaagctcaaccgcagcgaggcctacatcgcgg agaacgtgctggccctggacatcttctttgaggccctcaactatgaga ccgtggagcagaagaaggcctatgagatgtcagagctgcttggtgaca ttgggggcagatggggctgttcatcggggccagcctgctcaccatcc tcgagatcctagactacctctgtgaggtgttccgagacaaggtcctgg gatatttctggaaccgacagcactcccaaaggcactccagcaccaatc tgcttcaggaagggctgggcagccatcgaacccaagttccccacctca gcctgggccccagacctcccacccctccctgtgccgtcaccaagactc tctccgcctcccaccgcacctgctaccttgtcacacagctctagacct gctgtctgtgtcctcggagccccgccctgacatcctggacatgcctag cctgcacgtagcttttccgtcttcaccccaaataaagtcctaatgcat cagc The target sequence on mouse ASIC3 mRNA for
miRNA844 (510-531 relative to start site
of mouse ASIC3)
                                  (SEQ ID NO: 17)
CUUCAAGAGUCCAGGUGUCCC The target sequence on mouse ASIC3mRNA for miRNA847
(259-279 relative to start site of mouse ASIC3)
                                  (SEQ ID NO: 18)
AUGUGUUUCACUGUCGACCCU The target sequence for human miRNA 847
(256-276 relative to start site of human ASIC3 )
                                  (SEQ ID NO: 19)
ACGUGUCCCACUGUCGGCCCU The target sequence for human miRNA 844
(507-528 relative to start site of human ASIC3)
                                  (SEQ ID NO: 20)
ACUUCAAGAGUCCGGGUGUUCC The DNA sequence of the active moiety of miRNA 844
                                  (SEQ ID NO: 21)
TGAAGTTCTCAGGTCCACAGGG

EXAMPLES

The present invention is further defined in the following Examples, in which parts and percentages are by weight and degrees are Celsius, unless otherwise stated. The disclosure of each reference set forth herein is incorporated herein by reference in its entirety.

Example 1

ASIC1 and ASIC3 Play Different Roles in the Development of Hyperalgesia Following Inflammatory Muscle Injury Acid-sensing ion channels (ASICs) respond to acidosis that normally occurs after inflammation. We examined the expression of ASIC1, ASIC2, and ASIC3 mRNAs in lumbar DRG neurons before and 24 h after carrageenan-induced muscle inflammation. Muscle inflammation causes bilateral increases of ASIC2 and ASIC3, but not ASIC1 (neither ASIC1a nor ASIC1b) mRNA, suggesting differential regulation of ASIC1 versus ASIC2 and ASIC3 mRNA. Similar mRNA increases were observed following inflammation in knockout mice: ASIC2 mRNA increases in ASIC3−/− mice; ASIC2 and ASIC3 mRNAs increase in ASIC1−/− mice. Prior behavioral studies in ASIC3−/− mice showed deficits in secondary hyperalgesia (increased response to noxious stimuli outside the site of injury), but not primary hyperalgesia (increased response to noxious stimuli at the site of injury). In this study, we show that ASIC1−/− mice surprisingly do not develop primary muscle hyperalgesia, but develop secondary paw hyperalgesia. In contrast and as expected, ASIC3−/− mice develop primary muscle hyperalgesia, but do not develop secondary paw hyperalgesia. The pharmacological utility of the non-selective ASIC inhibitor A-317567, given locally, was tested. A-317567 reverses both primary and the secondary hyperalgesia induced by carrageenan muscle inflammation. Thus, peripherally located ASIC1 and ASIC3 play different roles in the development of hyperalgesia after muscle inflammation.

Example 2

Perspective

This study shows changes in ASIC mRNA expression and behavioral hyperalgesia of C57Bl/6 (wild type), ASIC1−/−, and ASIC3−/− mice before and after the induction of muscle inflammation. A-317567 was effective in reversing hyperalgesia in these animals, suggesting the potential of ASICs as therapeutic targets for muscle inflammatory pain.

Example 3

Introduction

Acid-sensing ion channels (ASICs) are proton-gated voltage-independent ion channels located on neurons in the peripheral and central nervous systems. ASICs belong to the epithelial sodium channel/degenerin (ENaC/DEG) family of amiloride-sensitive transmembrane ion channel proteins (see[37, 41, 78]). Four genes within mammalian genomes encode seven subunits to date—ASIC1a, ASIC1b, ASIC1b2, ASIC2a, ASIC2b, ASIC3 and ASIC4.[1, 15, 26, 27, 40, 54, 69, 73] Homomeric and heteromeric ASIC subunits combine to form trimeric ASICs,[13, 34] which depending on the subunit composition in the DRG display differences in pH sensitivity, current kinetics and ion selectivity.[11, 20, 29, 53] ASICs respond to acidosis, play a significant role in nociceptive processing of hyperalgesia both peripherally and centrally.[1, 3, 6, 8-10, 15, 16, 21, 27, 28, 37, 40-42, 54, 65, 66, 68, 70, 72-74, 76]

Despite a number of well-designed and controlled studies, the role of ASICs in nociception has led to conflicting results. Some prior behavioral studies generated from ASIC knockout or dominant negative mutant mice show no differences or increases in hyperalgesia of the paw after intraplantar inflammation.[16, 45, 56, 68] Previous studies show increases in ASIC1, ASIC2, and ASIC3 mRNAs after cutaneous paw inflammation[30, 71]. Our laboratory, however, has consistently shown that ASIC3 plays a critical role in the development of inflammatory and non-inflammatory hyperalgesia induced by deep tissue insult,[30, 65, 66] which Yen et al. also reported recently[81] We have suggested that these differences could be related to differences between cutaneous and deep tissue injury. However, differences between pain at the site of injury, termed primary hyperalgesia, and pain outside the site of injury, termed secondary hyperalgesia, could also explain these differences. Animal models of cutaneous inflammation typically measure primary hyperalgesia at the paw; while those of deep tissue insult have typically measured secondary hyperalgesia at the paw. One purpose of this study was to determine if there were differences in expression of ASICs with deep tissue inflammation, and behavioral deficits in ASIC1 and ASIC3 knockout mice with regard to primary and secondary hyperalgesia after muscle insult.

Animal models of pain have not sorted out whether ASICs play a peripheral or central role in the continued manifestation of the hyperalgesia after the inflammation is established. Previous literature suggests that peripherally located ASIC3 is important at the site of muscle inflammation since re-expression of ASIC3 into muscle of ASIC3-/- mice prior to induction of inflammation restores the hyperalgesia.[66] Co-administration of the ASIC3 antagonist, APETx2 with CFA into the paw prevents the development of cutaneous hyperalgesia 4 h later in rats, whereas blockade of peripheral ASIC1 with Psalmotoxin 1(PcTx1) at the time of intraplantar CFA injection has no effect on cutaneous hyperalgesia.[21] Intrathecal or intracerebroventricular blockade of ASIC1 induces analgesia and reverses hyperalgesia after nerve injury.[21, 44] Systemic application of the non-selective antagonists A-317567 and amiloride reduce primary hyperalgesia induced by CFA and skin incision.[24] In this study, we therefore used a non-selective inhibitor of ASICs, A-317567, injected directly into the muscle 24 h after muscle inflammation to test if activation of peripheral ASICs were important in maintaining hyperalgesia. We further tested the effectiveness of this drug in ASIC1-/- and ASIC3-/- mice to examine whether ASIC1 or ASIC3 were critical for the behavioral effects.

We therefore hypothesized that there would be differential expression of ASICs after inflammation, and that ASIC3, but not ASIC1, would mediate the secondary hyperalgesia associated with muscle inflammation. Since there were behavioral deficits in both ASIC1-/- and ASIC3-/- mice, we tested the ability of A-317567 to reverse both primary and secondary hyperalgesia in WT and in ASIC3-/- and ASIC1-/- mice with muscle inflammation.

Example 4

Methods

Animal Care and Use

All animal experiments were approved by the University of Iowa Animal Care and Use Committee and were conducted in accordance with National Institutes of Health guidelines. Congenic ASIC1-/- and ASIC3-/- on a C57Bl/6 background and congenic C57Bl/6 (WT) mice were bred at the University of Iowa Animal Care Facility.[56, 76] New breeding pairs of mice are started every six months. The congenic ASIC1-/- is a knockout of ASIC1a, and not ASIC1b.[76] Male and female mice, 6-10 weeks of age, WT (n=64), ASIC3-/- (n=32), ASIC1-/- (n=24) were used in these studies.

Induction of Inflammation

Mice were briefly anesthetized with 4% isoflurane and one gastrocnemius muscle (left) was injected with 20 µl of 3% carrageenan dissolved in sterile isotonic saline, which has a slightly acidic pH (6.0), typical of commercially available saline preparations. The pH of the final 3% carrageenan solution was 6.0. Behavior measurements were made before and 24 hours after carrageenan injection, and after administration of drug, A-317567.

A-317567

Mice were given one dose of 0.025 µmol A-317567 (C-{6-[2-(1-isopropyl-2-methyl-1,2,3,4-tetrahydro-isoquinolin-7-yl)-cyclopropyl]-naphthalen-2-yl}-methanediamine) (10 µl) injected into the left gastrocnemius muscle 24 hours after induction of inflammation. As a control for systemic effects one group of WT mice (n=8) received 0.025 µmol A-317567 (10 µl) in the contralateral muscle. Isotonic saline (10 µl) was used as the vehicle control in separate mice (n=45). Animals were tested 15 minutes after administration of the drug or vehicle.

Behavioral Testing

Mice were acclimated for 2 days before testing for muscle sensitivity and cutaneous mechanical sensitivity, as described previously.[30] Muscle sensitivity was tested by squeezing the gastrocnemius muscle of the mice with a calibrated pair of tweezers until the mouse withdrew from the stimulus. The force at which the mouse withdrew was measured in mN. A decrease in threshold was interpreted as primary hyperalgesia. Sensitivity in both the ipsilateral and contralateral muscles was measured. Muscle sensitivity was tested as follows: before carrageenan injection of the muscle, 24 h after the injection, and 15 min after A-317567 injection. Baseline responses for muscle sensitivity for WT, ASIC1-/-, and ASIC3-/- mice did not differ significantly, and baseline responses were similar for left and right sides. Cutaneous mechanical sensitivity was tested bilaterally by assessing the number of responses to repeated application of a 0.4 mN von Frey filament to the plantar surface of the paw. The number of withdrawals out of 5 was assessed in 10 trials and an average of all 10 trials was determined for each time period. A significant increase in the number of responses was interpreted as secondary mechanical hyperalgesia. Cutaneous mechanical sensitivity was tested as follows: before carrageenan injection of the muscle, 24 h after the injection, 15 min after A-317567 injection. Testing was blinded for genotype and drug status of the animals. WT, ASIC1-/-, and ASIC3-/- mice did not differ in baseline cutaneous mechanical sensitivity responses.

Quantitative RT-PCR

RNA was purified from ipsilateral and contralateral lumbar (L4, L5, L6) DRGs using the Trizol reagent (Invitrogen, Carlsbad, Calif.). DRGs were collected 24 h after carrageenan injection or from control mice. All of the mice were subjected to behavioral testing for muscle and cutaneous mechanical sensitivity 1-2 hours prior to collecting the DRGs. RNA concentration and purity was assessed by spectrophotometric measurement at 260 and 280 nm. First strand cDNA was synthesized from 0.2-1 ug of each RNA sample using Superscript III or VILO reverse transcriptase (Invitrogen, Carlsbad, Calif.). Taqman PCR was carried out using an ABI prism 7900 sequence detector (Applied Biosystems, Inc., Foster City, Calif.) on diluted cDNA samples (University of Iowa, DNA Facility, Iowa City, Iowa). Reactions were carried out for 40 cycles in triplicate. ASIC1 (ASIC1a and ASIC1b) (Mm01305997_m1), ASIC2 (Mm00475691_m1), ASIC3 (Mm00805460_ml) and the mouse control assay for glyceraldehyde-3-P-dehydrogenase (GAPDH) were obtained from Applied Biosystems, Inc. (Foster City, Calif.). All of the assays would generate a single PCR product which spans the boundary of two exons, thus reducing the possibility of genomic DNA contamination in the results. Control samples without reverse transcriptase did not produce any background PCR products. Quantitative RT-PCR data were normalized with GAPDH mRNA levels and relative amounts of mRNA were determined by using the comparative cycle thresholds ($C_T$).

Statistical Analysis

Data are represented as the mean±S.E.M. Behavioral data were analyzed with a repeated measures ANOVA followed by post-hoc testing with a Tukey's test. Differences were considered significant at $p<0.05$. Quantitative RT-PCR was analyzed with a two-way ANOVA for group (WT, WT-inflamed, ASIC1–/–, ASIC3–/–) and side (ipsilateral vs. contralateral).

Example 5

Figure 2:
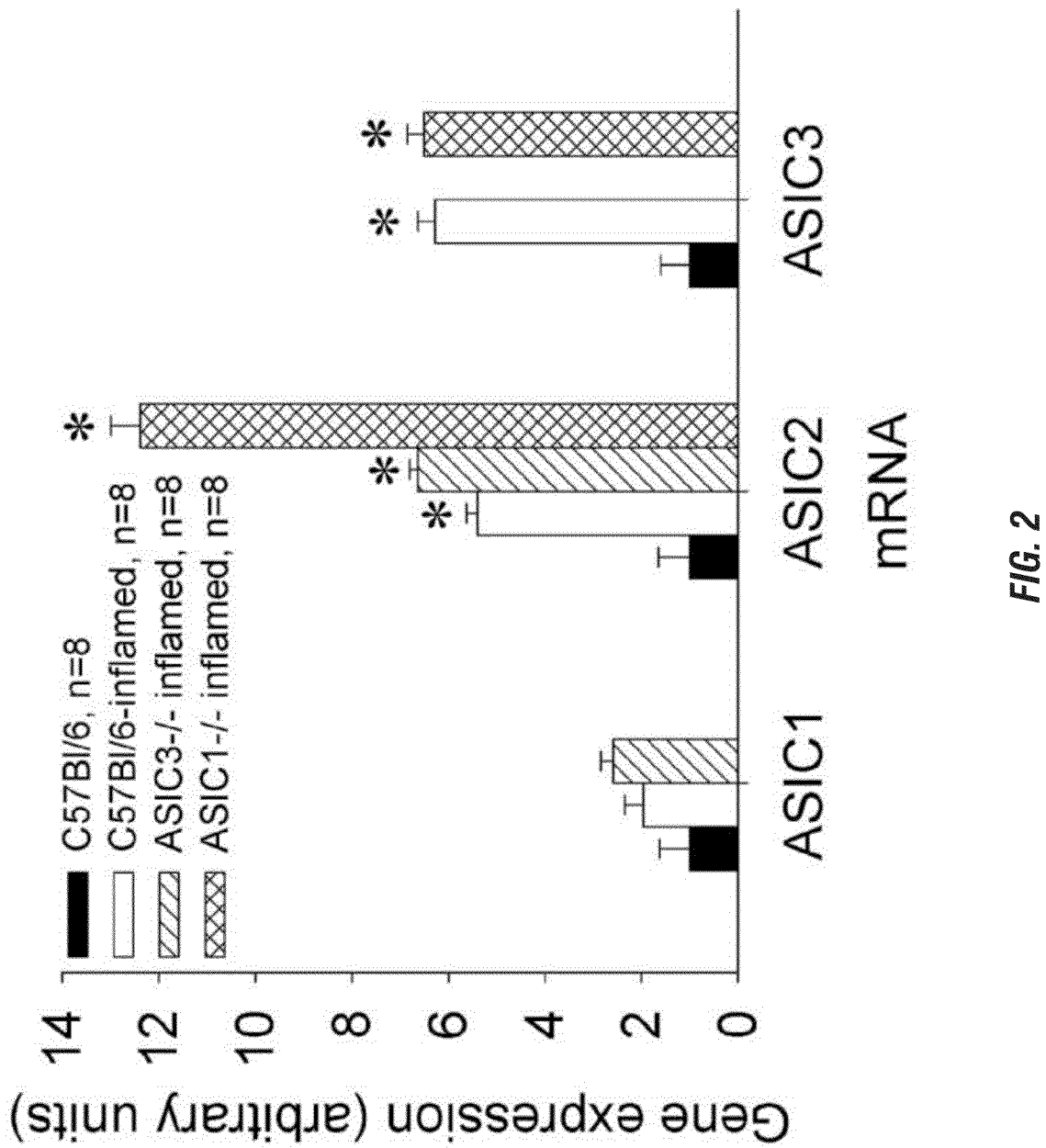
FIG. 2. shows comparative qRT-PCR analysis for ASIC1, ASIC2, and ASIC3 mRNAs in L4, L5, and L6 DRGs from C57Bl/6, C57Bl/6-inflamed, ASIC3−/− inflamed, and ASIC1−/− inflamed mice. ASIC2 mRNA was increased in C57Bl/6-inflamed, ASIC3−/− inflamed and ASIC1−/− inflamed mice. ASIC3 mRNA increased in C57Bl/6-inflamed and in ASIC1−/− inflamed mice. ASIC1 mRNA levels were not significantly different between the groups. (*=significantly increased from C57Bl/6 uninflamed mice, P<0.05).

Increased Expression of ASIC2 and ASIC3 but not ASIC1 mRNA in DRG After Muscle Inflammation There is a significant induction (approximately 10-fold increases) of ASIC2 and ASIC3, but not ASIC1 (ASIC1a and ASIC1b) mRNA in the lumbar DRG innervating muscle 24 h following carrageenan-induced muscle inflammation when compared to DRG from mice without muscle inflammation (FIG. 1). Statistical analysis showed a significant effect for inflammation for ASIC2 ($F_{1,40}=13.7$, $p=0.001$) and ASIC3 ($F_{1,32}=13.7$, $p=0.001$) but not ASIC1. However there was no effect for side (ipsilateral or contralateral) indicating a bilateral increase in mRNA in the DRG after unilateral muscle inflammation. Since there was not a significant difference between the results for the ipsilateral and contralateral mRNAs, the data for the two sides were pooled graphically. Twenty-four hours after carrageenan-induced muscle inflammation, ASIC3–/– mice showed increases in ASIC2 mRNA (6-fold) and ASIC1–/– mice showed increases in ASIC2 and ASIC3 mRNAs, at 12- and 6-fold, respectively; these increases were not significantly different from WT mice (FIG. 2). Thus, ASIC2 and ASIC3 increased with inflammation and ASIC1 did not, suggesting a differential regulation of ASICs.

Example 6

Hyperalgesia of the Muscle does not Develop in ASIC1–/– Mice

Figure 3:
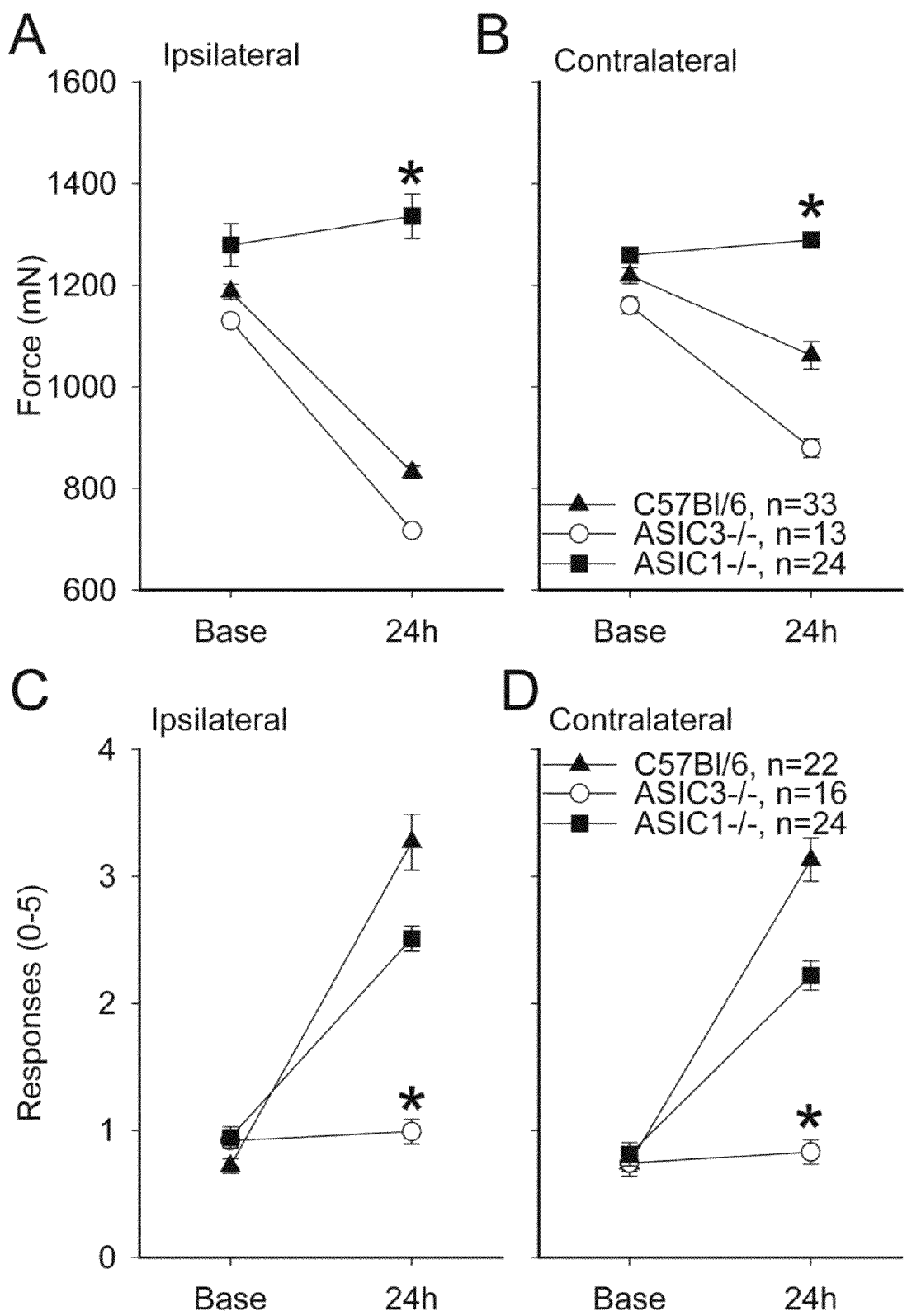
FIGS. 3A and B) Muscle hyperalgesia (tweezers) develops similarly in both C57Bl/6 (WT) and ASIC3−/− mice after muscle inflammation on both ipsilateral and contralateral sides. ASIC1−/− mice do not develop muscle hyperalgesia after muscle inflammation. C and D) Cutaneous mechanical hyperalgesia (von Frey) develops similarly in both C57Bl/6 (WT) and ASIC1−/− mice on both sides. Cutaneous hyperalgesia does not develop in ASIC3−/− mice after muscle inflammation. (*=P<0.05).

C57Bl/6 (WT) mice showed a significant bilateral decrease in the withdrawal threshold of the muscle 24 h after carrageenan-induced muscle inflammation; the decrease was greater for the ipsilateral inflamed muscle compared to the contralateral muscle ($p<0.05$) (FIGS. 3A and B). A similar decrease in withdrawal threshold of the muscle was observed in ASIC3–/– mice 24 h after muscle inflammation (FIGS. 3A and B). Muscle withdrawal thresholds in ASIC1–/– mice, however, were unchanged 24 h after carrageenan-induced muscle inflammation, on both the ipsilateral or contralateral sides, and the withdrawal thresholds were significantly greater than WT mice ($P<0.05$).

Example 7

Hyperalgesia of the Paw does not Develop in ASIC3–/– Mice

C57Bl/6 (WT) mice showed a significant bilateral increase in the number of withdrawals to a 0.4 mN force applied to the paw 24 h after carrageenan-induced muscle inflammation (FIGS. 3C and D). There was a similar increase in the number of withdrawals for both the ipsilateral and contralateral paws of ASIC1–/– mice 24 h after carrageenan-induced muscle inflammation (FIGS. 3C and D). However, ASIC3–/– mice showed a significant reduction ($p<0.05$, compared to C57Bl/6 (WT) mice) in the number of withdrawals on both the ipsilateral and contralateral sides 24 h after muscle inflammation (FIGS. 3C and D) in agreement with a prior study.[66]

Example 8

A-317567 Reverses Muscle and Paw Hyperalgesia

Figure 4:
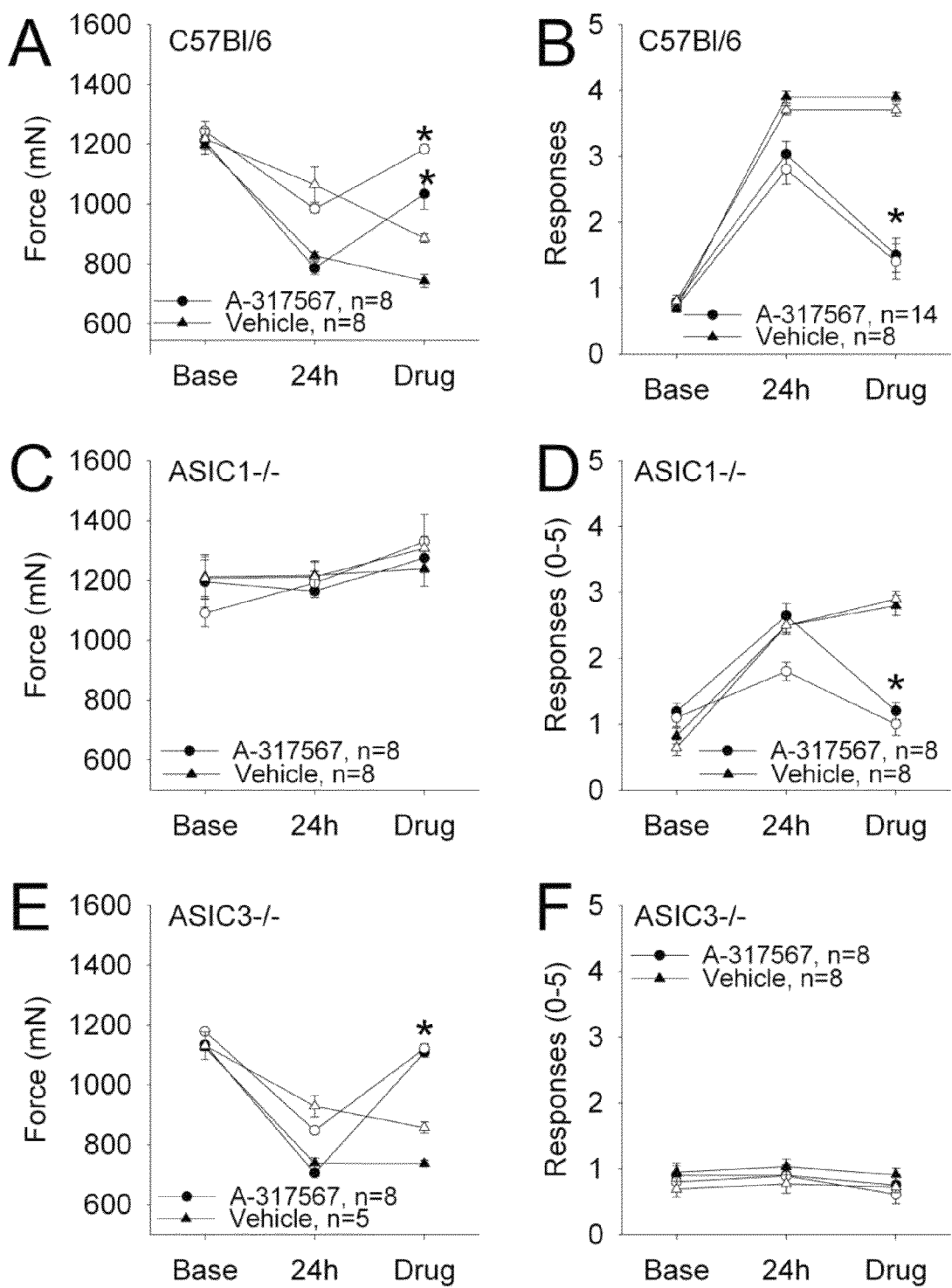
FIG. 4. shows the effect of A-317567, non-selective ASIC antagonist, on muscle inflammation in C57Bl/6 (WT), ASIC1−/− and ASIC3−/− mice. A, C and E Muscle sensitivity (tweezers) in mice before and 24 h after carrageenan-induced muscle inflammation, and after A-317567 treatment. B, D and F Cutaneous mechanical sensitivity before and after muscle inflammation, and after A-317567 treatment. Closed symbols=ipsilateral, open symbol=contralateral sides. C57Bl/6 (WT) mice (A and B) develop muscle hyperalgesia (tweezers) (A) and cutaneous mechanical hyperalgesia (B) 24 h after carrageenan-induced muscle inflammation and is reversed by A-317567. Hyperalgesia and reversal with A-317567 is seen in both the ipsilateral and contralateral sides. ASIC1−/− mice (C and D), do not develop muscle hyperalgesia after muscle inflammation and A-317567 has no effect on muscle withdrawal thresholds (C). Cutaneous mechanical hyperalgesia develops in ASIC1−/− mice after muscle inflammation and A-317567 reverses the hyperalgesia on both sides (D). ASIC3−/− mice (E and F) develop muscle hyperalgesia after muscle inflammation and A-317567 reverses the effect on both ipsilateral and contralateral sides (E). A-317567 has no effect on mechanical responsiveness in ASIC3−/− mice that do not develop mechanical hyperalgesia after muscle inflammation (F). (*=P<0.05 when compared to the vehicle).

To determine if ASICs are important for maintaining hyperalgesia once developed, we next tested if peripheral blockade of ASICs would reverse the hyperalgesia in C57Bl/6 mice. Injection of 0.025 μmole A-317567, a non-selective ASIC antagonist, into the inflamed gastrocnemius muscle (24 h after inflammation) reversed the decrease in muscle withdrawal threshold in C57Bl/6 (WT) (FIGS. 4A and B). Surprisingly, the unilateral injection of A-317567 reversed the hyperalgesia on both the ipsilateral and the contralateral sides. To confirm that this dose did not produce a systemic effect, we injected 0.025 μmol A-317567 into the contralateral gastrocnemius muscle of animals with carrageenan induced inflammation of the ipsilateral muscle. The withdrawal thresholds of both sides remained unchanged 15 min after injection of the drug into the contralateral gastrocnemius muscle (798±31 mN ipsilateral; 990±50 mN contralateral), which is comparable to the withdrawal thresholds prior to drug administration (880±24 mN ipsilateral; 1128±40 mN contralateral) in WT mice with muscle inflammation of the ipsilateral gastrocnemius muscle.

To further confirm the role of ASIC1 in muscle sensitivity and ASIC3 in cutaneous sensitivity we tested the effect of A-317567 in ASIC3–/– and ASIC1–/– mice, respectively. In ASIC1–/– mice where there is an increased number of withdrawals to mechanical stimulation of the paw, unilateral intramuscular injection of 0.025 μmol A-317567, 24 h after carrageenan induced muscle inflammation, decreases the number of withdrawals bilaterally (FIG. 4D), However, in ASIC1–/– mice that do not show a decrease in muscle withdrawal threshold after inflammation, A-317567 had no effect (FIG. 4C). In contrast, in ASIC3–/– mice intramuscular injection of 0.025 μmole A-317567 reduces the inflammation-induced decrease in withdrawal threshold of the muscle (FIG. 4E). However, in ASIC3–/– mice, where there is no change in the number of withdrawal thresholds of the paw to mechanical stimulation, at 24 h after carrageenan induced muscle inflammation, A-317567 has no effect (FIG. 4F).

Example 9

Bilateral Changes in ASIC Expression after Injury

The current study shows an upregulation of ASIC2 and ASIC3 mRNAs in lumbar DRGs following muscle inflammation, not only ipsilateral to the inflamed muscle, but also contralaterally. Surprisingly, the bilateral increases in mRNAs were of similar magnitude, despite a unilateral muscle inflammation, and a greater hyperalgesia ipsilaterally. This is a uniquely different pattern to that observed after cutaneous inflammation induced by CFA injection where increases were observed unilaterally for ASIC1a, ASIC1b, ASIC2b, and ASIC3.[71] The differences between the magnitude of hyperalgesia and mRNA levels could be the result of protein modification and interactions ipsilaterally in the inflamed tissue. Inflammatory mediators and protein phosphorylation can modulate and enhance ASIC currents.[2, 31, 38, 71] Thus, although mRNA levels are similar bilaterally, there could be enhanced ASIC activity ipsilaterally from the inflamed muscle that would be manifested as a greater degree of hyperalgesia.

Similar to the results with mRNA expression, local blockade of ASICs with A-317567 reversed the hyperalgesia not only on the injected side, but also on the contralateral side. The reversal of hyperalgesia in knockout mice was specific for ASIC1 and muscle hyperalgesia, and for ASIC3 and paw hyperalgesia, whether ipsilateral or contralateral to the inflamed muscle. The bilateral effect was unexpected but suggests activation of ASICs in inflamed muscle is critical for maintaining hyperalgesia through enhancing central excitability. In support of a role for ASICs in central sensitization, dorsal horn neurons from ASIC3-/- mice do not develop enhanced central excitability that normally occurs after repeated intramuscular acid injection.[65]

The bilateral increases in expression of mRNA for ASIC in the lumbar DRG following muscle inflammation could result from generation of dorsal root reflexes (DRR) bilaterally. Dorsal root reflexes are antidromic action potentials generated at the central terminals of primary afferent fibers, which then result in peripheral release of inflammatory mediators to enhance inflammation and pain.[67] Previously we showed that carrageenan-induced inflammation generates DRRs at the level of the spinal cord that enhance the inflammatory process ipsilaterally.[57, 63, 64] Unilateral inflammation also produces DRRs not only on the ipsilateral side, but also the contralateral side.[12, 36, 58] There are also measurable bilateral effects indicative of inflammation such as edema, vasodilation and plasma extravasation.[36, 58] Thus, we conclude that unilateral muscle inflammation results in the generation of DRRs ipsilaterally and contralaterally that then increases expression of ASIC mRNAs in both the ipsilateral and contralateral DRGs. Bilaterally increased expression of ASIC mRNAs in the DRGs could result in increased sensitivity to peripherally applied stimuli manifested as hyperalgesia. Blocking input from the inflamed muscle, with the local injection of A-317567 into the ipsilateral side, would prevent this input from reaching the spinal cord to generate the central excitability and dorsal root reflexes.

With muscle inflammation, WT, ASIC1-/-, and ASIC3-/- mice showed a significant upregulation of ASIC2 mRNA. We propose that ASIC2 might modulate channel activity. In cell culture experiments, ASIC2/ASIC3 heteromeric channels demonstrate increased responses to decreased pH over that of ASIC3 homomeric channels[7] and ASIC2a enhances ASIC1a's response to the regulatory neuropeptide FMRFamide.[5] In our studies, the ASIC1 mRNA levels in the lumbar DRGs before and after inflammation remain unchanged. Our mRNA data suggest that ASIC1, ASIC2, and ASIC3 are differentially regulated with inflammation.

Example 10

ASIC 1 and ASIC3 Play Distinct Roles in Muscle and Cutaneous Hyperalgesia

Genetically modified knockout mice or transgenic animals for ASICs have not always demonstrated a positive result for their role in nociception after peripheral inflammation or acid injections.[22, 45, 49, 55, 56, 59, 68] Some prior literature focusing on ASIC3-/- mice show no difference or even enhanced hyperalgesia of the paw after paw inflammation, i.e. primary hyperalgesia.[16, 56, 68] However, the current study, and our prior studies consistently show deficits in secondary hyperalgesia after muscle or joint insult in ASIC3-/- mice,[65, 66] again suggesting differences between deep tissue hyperalgesia and cutaneous hyperalgesia.

We also show for the first time that muscle hyperalgesia at both the site of inflammation and the contralateral hindlimb does not develop in ASIC1-/- mice. This result is distinctly different from prior work showing that there is still increased mechanical hyperalgesia of the paw after carrageenan paw inflammation, and after repeated intramuscular acid injection.[65, 68, 81] We suggest the differences between the prior reports and the current study are directly related to differences between processing of cutaneous and muscle nociceptive information. Muscle afferents express more ASIC3, calcitonin gene-related peptide (CGRP), and substance P and less isolectin B4 and somatostatin when compared to cutaneous afferents.[46, 47, 52] Injection of neuropeptides into skin or muscle results in different responses. Substance P produces spontaneous pain when injected into skin and a decrease in the pressure pain threshold, without spontaneous pain, when injected into muscle.[35] CGRP does not produce pain when injected alone into either skin or muscle but produces pain when injected with substance P into muscle.[51] Centrally there are also differences in processing of nociceptive information from muscle when compared to skin. For example, stimulation of C-fibers innervating muscle produces prolonged discharges in flexor motor neurons that outlasts the stimulus, is longer lasting than cutaneous stimulation of C-fibers, and increases response to noxious stimuli bilaterally.[75, 79] Formalin injected into the skin of the lower back increases c-fos expression throughout laminae I-V, but when injected into the muscles of the lower back there is no labeling in laminae II.[48] Thus, differences in processing of nociceptive stimulation from skin and muscle likely underlie the differences between prior studies utilizing cutaneous models of inflammation and the current study using a model of muscle inflammation.

Differences in the tissue expression of ASIC subunits in peripheral neurons or peripheral tissues could influence nociceptive behavior. The current data shows that blockade of peripheral receptors with A-317567 at the site of inflammation reverses the muscle and cutaneous hyperalgesia once developed suggesting peripheral receptor activation is critical to the development of hyperalgesia. In addition to expression in sensory neurons and brain, ASIC3 is located in non-neuronal tissues such as testis, muscle, lung, bone and synovium.[6, 30, 32, 33] The role of ASIC3 in these non-neuronal cells is unclear but ASIC3 may also modulate nociception indirectly. ASIC1 is abundantly expressed in spinal cord neurons and brain,[1, 3, 6, 8-10, 15, 19, 27, 40, 54, 73, 74, 76-78, 80] and its action is thought to primarily be through central mechanisms. It is unclear if centrally expressed ASIC1a plays a distinct role in the processing of hyperalgesia after muscle inflammation. This study highlights the action of ASIC1 in the peripheral sensory neurons, since blockade of peripheral ASICs completely reverses the hyperalgesia once developed.

Example 11

Inhibition of ASICs Reduces Nociceptive Behaviors

The pharmacology of ASICs has been extensively studied with non-selective drugs such as amiloride and A-317567.[4, 14, 17, 18, 21, 24, 43, 50, 60, 70, 71] A-317567 produces a concentration dependent inhibition of acid-evoked ASIC currents in DRG neurons[24, 39]. Intramuscular injection of amiloride also prevents the onset of hyperalgesia induced by repeated intramuscular acid injections suggesting ASIC3 and ASIC1 are important for mediating peripheral nociception at the site of injury.[65, 66] Re-expression of ASIC3 in primary afferent fibers innervating muscle of ASIC3−/− mice restores the mechanical hyperalgesia of the paw,[66] supporting a peripheral role for ASICs in deep tissue hyperalgesia.

In this study, blockade of ASICs in the inflamed muscle reverses the inflammation-induced hyperalgesia bilaterally. In contrast, we previously showed that intramuscular lidocaine in rats reversed carrageenan-induced muscle hyperalgesia ipsilaterally, but not contralaterally[61] This difference is surprising since lidocaine should reduce all afferent input to the spinal cord. However, differences could be related to the mode of action of the drug (specific blockade of ASICs vs. sodium channels), differences in hyperalgesia between mice and rats, or the magnitude of the change and power in the previous study (3 vehicle and 7 lidocaine) compared to the current study (8 vehicle and 8 A-317567).

Prior reports suggest that ASIC1 plays a role in the generation of hyperalgesia through the central nervous system.[44] Intrathecal application of amiloride or the ASIC1 antagonist PcTx1, however, prevents development of nocifensive behaviors that develop after formalin, acetic acid, glutamate, nerve injury, and repeated intramuscular acid injections.[25, 44, 62] Intrathecal delivery of siRNA to ASIC1a or ASIC3 prevents development of hyperalgesia induced by paw inflammation.[21, 23, 24] However our data show a reversal of muscle hyperalgesia with local injection of A-317567 in WT and ASIC3−/− mice, suggesting that ASIC1 at the site of muscle inflammation is important in the generation of muscle inflammation. While prior data support a central role for ASIC1, our data for the first time show a peripheral role of ASIC 1 in the generation of hyperalgesia.

In summary, growing bodies of evidence indicate that ASICs play a role in the sensory signaling associated with inflammatory pain. In this study, we find that ASIC1 and ASIC3 play distinct roles in the development of muscle inflammatory hyperalgesia. Analgesics targeted to specific subunits of ASICs may be useful in alleviating inflammatory muscle pain. Pharmaceuticals designed to reduce ASIC1a could result in decreases in pain at the site of muscle inflammation. Inhibitors of ASIC3 could reduce the development of secondary hyperalgesia, and referred pain following inflammation.

Example 12

Figure 5:
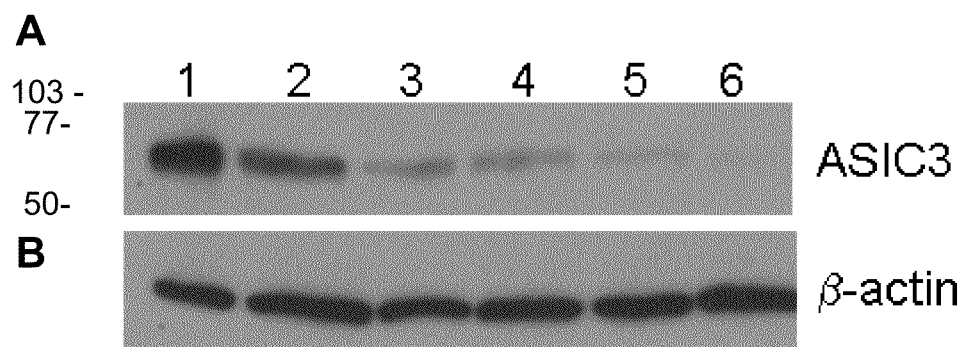
FIG. 5 shows the dose-dependent inhibition of ASIC3 expression by miRNA844 by Western blot analysis. CHO cells transfected with HA-tagged ASIC3 were exposed to increasing concentrations of miRNA-containing plasmid of 0, 8, 12, 16, 20, and 24 µg. Equal amounts of protein (20 µg) from the cell lysates were run on SDS-PAGE gels, transferred to nitrocellulose, probed with antibodies, and developed for peroxidase. Lanes 1 to 6 in Part A were probed with anti-HA-HRP whereas in Part B they were probed with rabbit anti-beta actin, and goat anti-rabbit HRP. The results show a progressive inhibition of ASIC3 expression with increasing concentration of miRNA containing plasmid.

Protocols have also been proposed for local or site directed deletion of ASICs at sensory endings or restoration of response (rescue) in ASIC knockout mice. In this invention we used 4 different sets of oligonucleotides 844, 845, 846, and 847, designed to generate miRNA sequences against mouseASIC3. These miRNAs, were cloned into the Invitrogen Gateway plasmid, pcDNA6.2-GW EmGFP-miR. The DNA sequence of each construct was verified by bidirectional DNA sequencing. The resultant constructs were chosen because they make large amounts transcript from the CMV Pol II promoter, and also co-express emerald GFP. When used in mammalian cell transfection studies, the cells which have taken up the plasmids are easily identified by fluorescence Each of the 4 different miRNA plasmids were tested in CHO cells transfected with ASIC3 and each construct was able to inhibit more than 90% the expression of ASIC3, as determined by Western blot hybridization. FIG. 5 shows a Western blot analysis demonstrating a dose dependent inhibition of ASIC3 expression by miRNA844. CHO cells transfected with HA-tagged ASIC3 were exposed to increasing concentrations of miRNA-containing plasmid of 0, 8, 12, 16, 20, and 24 µg. Equal amounts of protein (20 µg) from the cell lysates were run on SDSPAGE gels, transferred to nitrocellulose, probed with antibodies, and developed for peroxidase. Lanes 1 to 6 in Part A were probed with anti-HA-HRP whereas in Part B they were probed with rabbit anti-beta actin, and goat anti-rabbit HRP. The results show a progressive inhibition of ASIC3 expression with increasing concentration of miRNA containing plasmid. We also have demonstrated that miRNA844 and miRNA847 selectively inhibits mouse ASIC3 and not mouse ASIC1 data not shown).

Example 13

Functional ASIC Experiments

Figure 6:
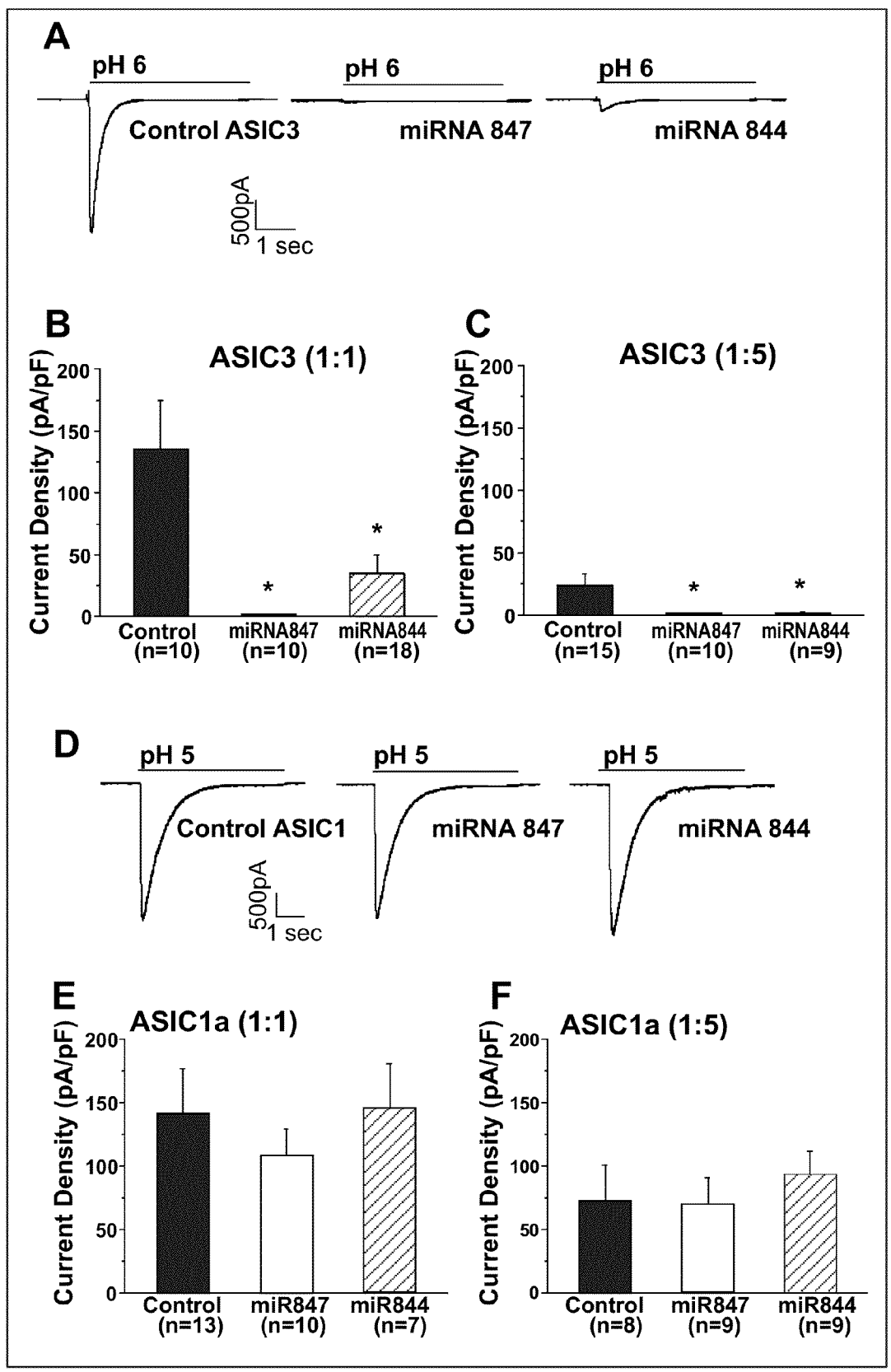
FIG. 6 shows functional ASIC current measurements in transfected CHO cells. A. shows an example of currents to pH 6.0 in CHO cells transfected with ASIC3 and the control miRNA, and two miRNAs directed against ASIC3, miRNA 847 and miRNA 844. B,C. shows the quantification of the effect of miRNA 847 and 844 on pH 6.0 currents in CHO cells transfected with ASIC3. *, significantly less than control; D. shows an example of currents to pH 5.0 in CHO cells transfected with ASIC1 and the control miRNA and the two miRNAs directed against ASIC3. E,F. Quantification of the pH effect on ASIC1 current by the ASIC3 miRNA. Notice that in B,C there is a significant reduction in ASIC3 currents by the ASIC3 miRNA, but there is no reduction in ASIC1 currents by the ASIC3 miRNA (E,F).

Effects of miRNAs to ASIC3 are specific for ASIC3 and not ASIC1 currents in transiently transfected CHO cells (FIG. 6) A. Whole cell ASIC3 currents from CHO cells expressing control miRNA, miRNA 847 and miRNA 844 respectively at pH 6. B. Current density of ASIC3 and control miRNA, miRNA 847 and miRNA844 transfected at 1 µg each at pH 6 (ASIC3: miRNA 1:1). C. Current density of ASIC3 and miRNAs at the concentration of (0.2 and 0.9 µg, respectively, I:5) studied at pH 6. D. Whole cell ASIC1 currents recorded from CHO cells in presence of miRNA control, 847 and 844 respectively at pH 5. E. Current density of ASIC1 currents at pH 5 in presence of miRNA control, miRNA 847 and miRNA 844.AS1C1 and miRNAs transfected at 1 µg each (1:1). F. Current density of ASIC1 and miRNAs transfected) at pH 5. ASIC1 and miRNAs transfected at a ratio of 1:5 (0.2 µg and 0.9 µg) respectively.

Example 14

In Vivo Experiments

Figure 7:
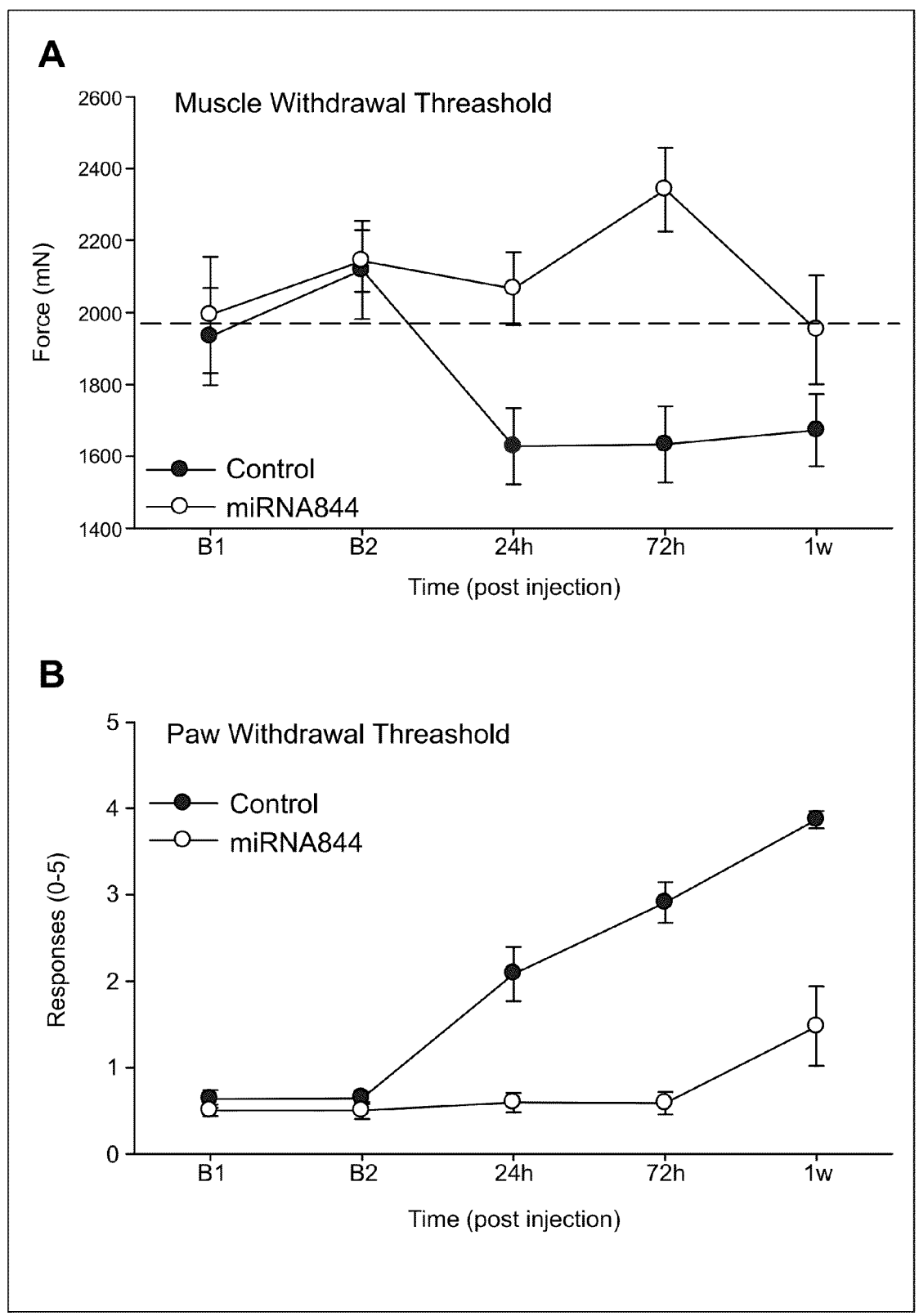
FIG. 7 shows in vivo injections of miRNA844 prevent the development of (A) primary (muscle withdrawal) and (B) secondary (paw withdrawal) hyperalgesia after carrageenan-induced muscle inflammation.

The two most effective inhibitory miRNA sequences against mouse ASIC3, 844 and 847 were inserted into the lentiviral vector, pLenti61VSDEST. The cloned sequences were verified by DNA sequencing. High titers (>$10^8$ PFU/mL) of these viruses were produced in the University of Iowa Vector Core Facility. The miRNAs against mouse ASIC3, 844 and 847, were also inserted in a herpes simplex viral (HSV) vector and high titers of virus was grown by Dr. Steven Wilson at the University of South Carolina. Twenty microliters of virus (lentivirus or HSV, miRNA or control) was injected into the left gastrocnemius muscle of C57B1/6Jmice. The mice were allowed to recover for 4 weeks. Behavior testing was conducted prior to the injection of virus, 4 weeks after injection, and 24 hours after carrageenan-induced muscle inflammation. We tested for changes in mechanical sensitivity, primary hyperalgesia, of the inflamed muscle; and for changes in mechanical sensitivity of the paw, secondary hyperalgesia. After muscle inflammation, there is increased sensitivity of both the muscle and the paw in control animals. FIG. 7 shows that mice injected with HSV containing miR-NAS44 did not develop this increased sensitivity of the muscle or the paw, i.e. primary or secondary hyperalgesia, respectively. The control HSV virus did not prevent the development of hyperalgesia.2600

Example 15

Inhibition of Human ASIC3

We cloned mRNA sequences against human ASIC3 by selecting nucleotide sequences that were targeted against homologous sequences to the regions targeted by mouse miRNA 844 and 847. These miRNAs were cloned in pcDNA6.2-GW ElnGFP-miR, and verified by DNA sequence analysis. Each of the miRNA containing plasmids (5 µg) was tested against CHO cells transfected with HA-tagged human ASIC3. We have shown that both miRNAs are effective at decreasing the expression of human ASIC3, as detected at the protein level by Western blotting. Beta-actin was probed as a control and was not inhibited by the miRNAs.

Example 16

Selective Targeting of ASIC3 Using miRNAs Results in the Inhibition of Primary and Secondary Hyperalgesia in Mice Our prior studies show that ASIC3−/− mice do not develop secondary mechanical hyperalgesia after non-inflammatory or inflammatory muscle insult, but develop primary hyperalgesia of the muscle. ASIC1a−/− mice do not develop primary hyperalgesia, but develop secondary hyperalgesia following carrageenan-induced muscle inflammation.

While ASIC knockout animals and ASIC antagonists are helpful in deciphering the role of ASICs in pain, we wanted to manipulate ASIC3 in primary afferents innervating the site of muscle injury to determine their role in the development of hyperalgesia.

We hypothesized that artificial miRNAs against ASIC3 would inhibit expression of ASIC3 in adult wild-type animals and prevent the development of inflammatory muscle hyperalgesia.

Artificial miRNAs.

Pre-miRNA sequences against mouse ASIC3 and against human ASIC3 were cloned into pcDNA6.2-GW EmGFP-miR (Invitrogen, Carlsbad, Calif.). The negative control miRNA (Invitrogen, Carlsbad, Calif.), which is not predicted to target any known mammalian gene, was also used. These miRNA sequences were tested in vivo as recombinant HSV-1 viruses (HSV-miRNA).

TABLE 3

| miRNA | pre-miRNA sequences | Target Sequence on ASIC3 RNA | Location of Target on ASIC3 |
|---|---|---|---|
| 844 | Top: GCTGTGAAGTTCTCAGGTCCA-CAGGGTTTTGGCCACTGACTGACCCTGTGGATGAGAACTTCA<br>Bottom: CCTGTGAAGTTCTCATCCACAGGGT-CAGTCAGTGGCCAAAACCCTGTGGACCTGAGAACTTCAC | CCCUGUGGACCUGA<br>GAACUUCA | 511-532 |
| 845 | Top: TGCTGTGGGCATGAAGCCAGGTGGTG-GTTTTGGCCACTGACTGACCACCACCTCTTCATGCCCA<br>Bottom: CCTGTGGGCATGAAGAGGTGGTGGT-CAGTCAGTGGCCAAAACCACCACCTGGCTTCATGCCAC | CACCACCUGGCUUC<br>AUGCCCA | 404-424 |
| 846 | Top: TGCTGAAACCATGCATCGTGCAGCTG-GTTTTGGCCACTGACTGACCAGCTGCAATGCATGGTTT<br>Bottom: CCTGAAACCATGCATTGCAGCTGGT-CAGTCAGTGGCCAAAACCAGCTGCACGATGCATGGTTTC | CAGCUGCACGAUGC<br>AUGGUUU | 69-89 |
| 847 | Top: TGCTGTACACAAAGTGACAGCTGG-GAGTTTTGGCCACTGACTGACTCCCAGCTCACTTTGTGTA<br>Bottom: CCTGTACACAAAGTGAGCTGGGAGT-CAGTCAGTGGCCAAAACTCCCAGCTGTCACTTTGTGTAC | UCCCAGCUGUCACU<br>UUGUGUA | 260-280 |
| Hu844 | Top: TGCTGTGAAGTTCTCAGGCCCACAAG-GTTTTGGCCACTGACTGACCTTGTGGGTGAGAACTTCA<br>Bottom: CCTGTGAAGTTCTCACCCACAAGGTCAGTCAGTGGCCAAAACCTTGTGGGCCTGAGAACTTCAC | CCUUGUGGGCCUGA<br>GAACUUCA | 508-529 |
| Hu847 | Top: TGCTGTGCACAGGGTGACAGCCGG-GAGTTTTGGCCACTGACTGACTCCCGGCTCACCCTGTGCA<br>Bottom: CCTGTGCACAGGGTGAGCCGGGAGT-CAGTCAGTGGCCAAAACTCCCGGCTGTCACCCTGTGCAC | UCCCGGCUGUCACC<br>CUGUGCA | 257-277 |

Artificial miRNAs directed against mASIC3 (miR-ASIC3) selectively inhibit protein expression of mASIC3 and acidic pH-evoked currents of ASIC3, and have no effect on protein expression or acidic pH-evoked currents of ASIC1a.

Figure 16:
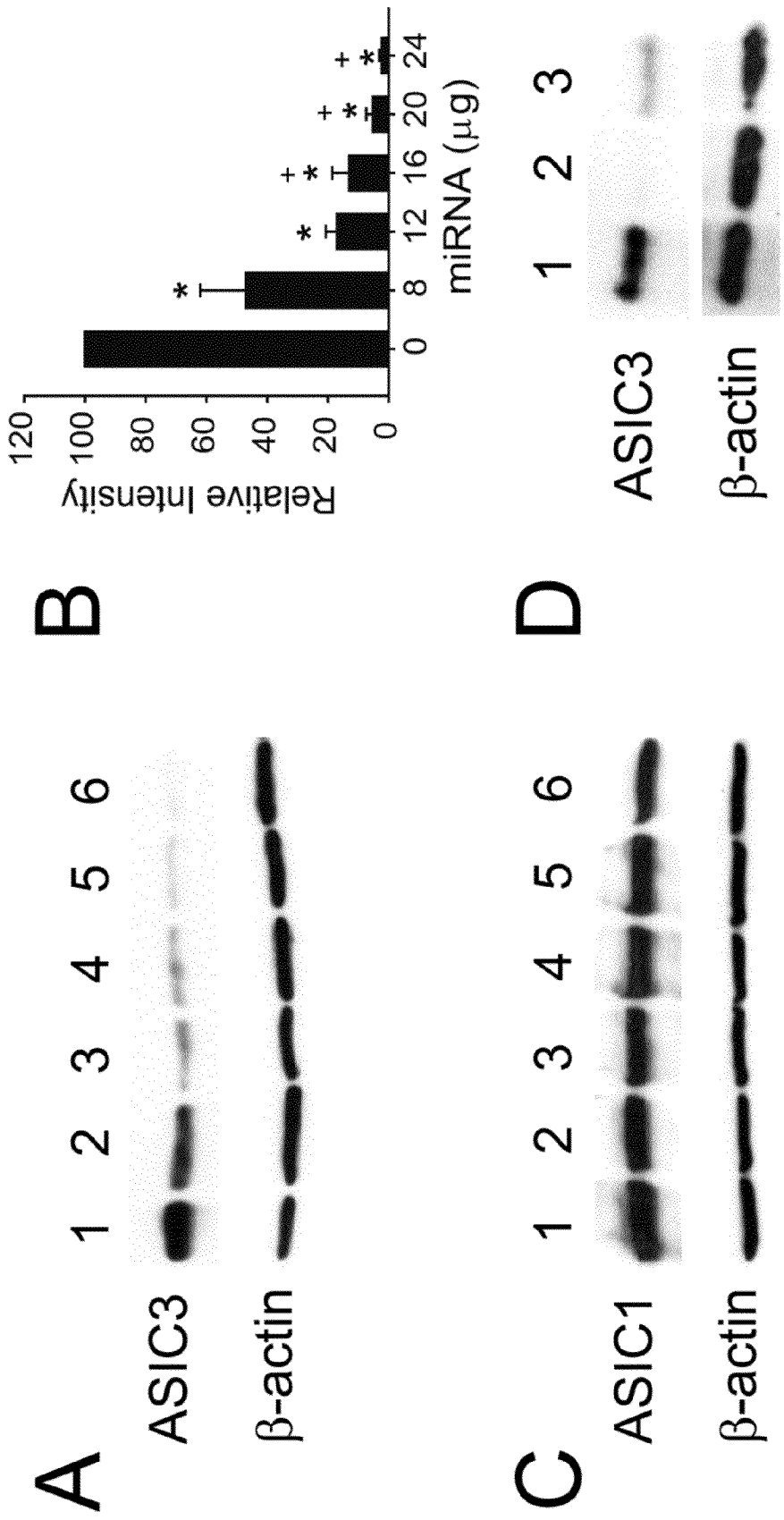
FIG. 16 shows a Western blot showing a dose-dependent inhibition of ASIC3 expression is shown in FIG. 15A. .HO-K1 cells were transfected with HA-tagged ASIC3 (4 µg) and increasing concentration of miR844-containing plasmid: 0, 8, 12, 16, 20, and 24 µg, lanes 1-6. B) Densitometric quantitation of ASIC3 protein levels show a significant reduction in ASIC3 protein (*p<0.0001; n=4 per miRNA concentration, significantly different form 0 µg miRNA group, +, p<0.05; significantly different from the 8 µg group). C) Western blot showing no inhibition of ASIC1a protein. HA-tagged ASIC1a (4 µg) plus 0, 10, 20 µg miR847 (lanes 1-3); HA-tagged ASIC1a plus 0, 10, 20 µg miR844 (lanes 4-6). D) Western blot showing inhibition of human ASIC3 protein. HA-tagged human ASIC3 (4 µg) plus 0, 5 µg human miR844 or 5 µg miR847 (lanes 1-3).

In FIG. 16A-D CHO-K1 cells were transfected with HA-tagged ASIC3 (4 µg) and increasing concentration of miR844-containing plasmid: 0, 8, 12, 16, 20, and 24 µg, lanes 1-6. FIG. 16A is a Western blot showing a dose-dependent inhibition of ASIC3 expression is shown in FIG. 16B Densitometric quantitation of ASIC3 protein levels show a significant reduction in ASIC3 protein (*p<0.0001; n=4 per miRNA concentration, significantly different form 0 µg miRNA group, +, p<0.05; significantly different from the 8 µg group).) 16C) Western blot showing no inhibition of ASIC1a protein. HA-tagged ASIC1a (4 µg) plus 0, 10, 20 µg miR847 (lanes 1-3); HA-tagged ASIC1a plus 0, 10, 20 µg miR844 (lanes 4-6). 16D) Western blot showing inhibition of human ASIC3 protein. HA-tagged human ASIC3 (4 µg) plus 0, 5 µg human miR844 or 5 µg miR847 (lanes 1-3).

Figure 17:
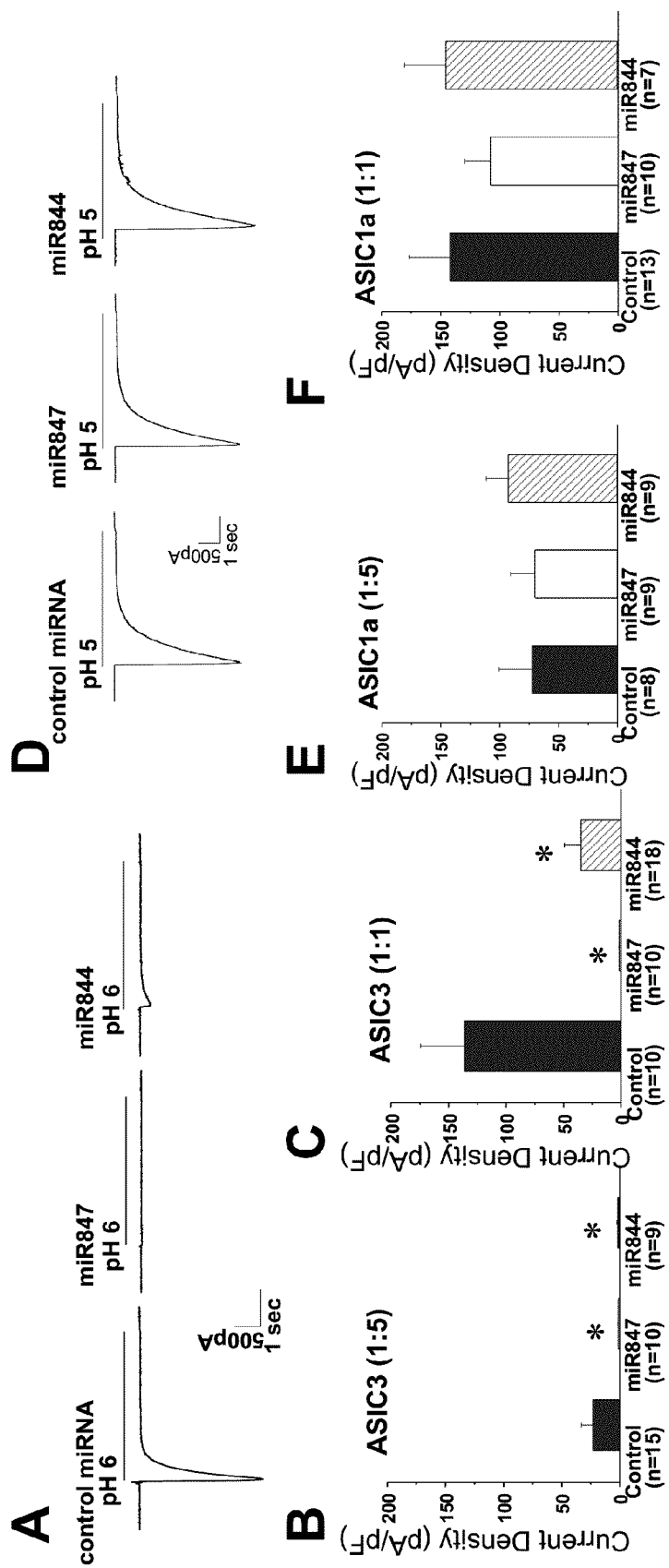
FIG. 17(A-F) are graphs which show that miR ASIC3 selectivity decreases ASIC3 surrent. A) Representative pH-evoked currents from CHO cells expressing ASIC3 along with control miRNA, miR847, or miR844. B) Mean pH 6-evoked current density from cells expressing ASIC3 and miRNAs transfected at 1:1 ratio *, significantly different from control miRNA. C) 1:5 ASIC3:miRNA ratio, *, significantly different from control miRNA. D) Representative pH-evoked currents from CHO cells expressing ASIC1a plus, control miRNA, miR847 or miR844. E) Mean pH-evoked current density from cells transfected at 1:1 ASIC1a:miRNA ratio, or F) at 1:5 ASIC1a:miRNA ratio.

Expression of ASIC3 in the DRGs is selectively inhibited after injecting recombinant HSV-1 viruses carrying miR-ASIC3 in vivo. FIG. 17. A) Representative pH-evoked currents from CHO cells expressing ASIC3 along with control miRNA, miR847, or miR844. B) Mean pH 6-evoked current density from cells expressing ASIC3 and miRNAs transfected at 1:1 ratio *, significantly different from control miRNA. C) 1:5 ASIC3:miRNA ratio, *, significantly different from control miRNA. D) Representative pH-evoked currents from CHO cells expressing ASIC1a plus, control miRNA, miR847 or miR844. E) Mean pH-evoked current density from cells transfected at 1:1 ASIC1a:miRNA ratio, or F) at 1:5 ASIC1a:miRNA ratio.

Animals injected intramuscularly with recombinant HSV-1 virus carrying miR-ASIC3 do not develop either primary (muscle) or secondary (paw) mechanical hyperalgesia following carrageenan induced muscle inflammation.

Figure 18:
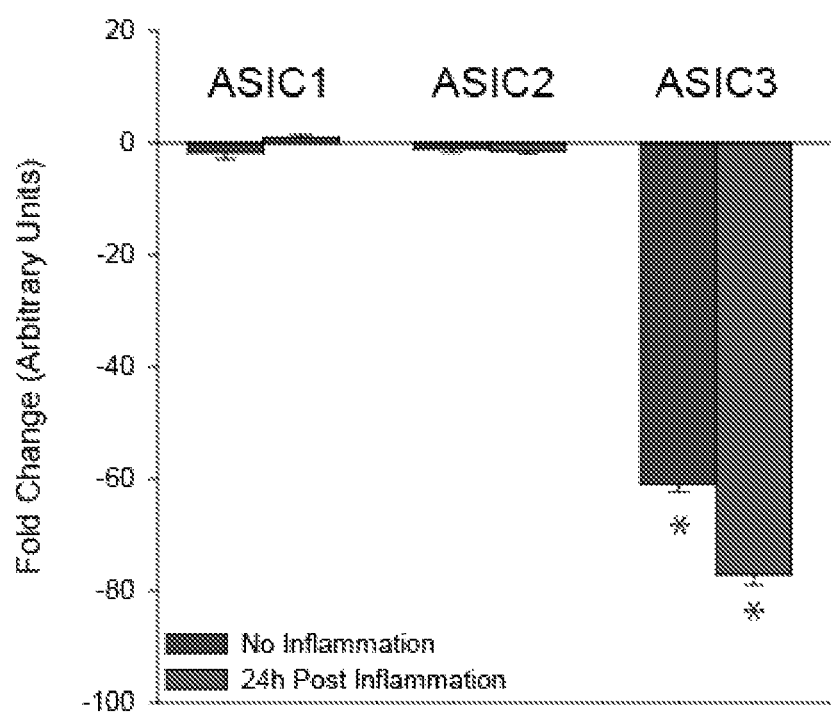
FIG. 18 is a graph showing that miR-ASIC3 selectively decreases ASIC3 mRNA expression. qPCR of ASIC1, ASIC2, and ASIC3 expression in ipsilateral DRGs (L4-6) from animals without inflammation and 24 h after carrageenan induced muscle inflammation (n=8 per group). Data are mean±S.E.M. of the fold change (2-ΔΔCT) in ASIC expression in HSV-miR844 versus HSV-control miRNA injected animals, normalized to GAPDH (*, P<0.05). Animals were injected with 200 of virus 107 PFU/ml into the left gastrocnemius muscle 4 weeks prior to testing. No changes in ASIC expression were detected in the contralateral DRGs.

FIG. 18. qPCR of ASIC1, ASIC2, and ASIC3 expression in ipsilateral DRGs (L4-6) from animals without inflammation and 24 h after carrageenan induced muscle inflammation (n=8 per group). Data are mean±S.E.M. of the fold change (2-ΔΔCT) in ASIC expression in HSV-miR844 versus HSV-control miRNA injected animals, normalized to GAPDH (*, P<0.05). Animals were injected with 20 µl of virus 107 PFU/ml into the left gastrocnemius muscle 4 weeks prior to testing. No changes in ASIC expression were detected in the contralateral DRGs.

Figure 19:
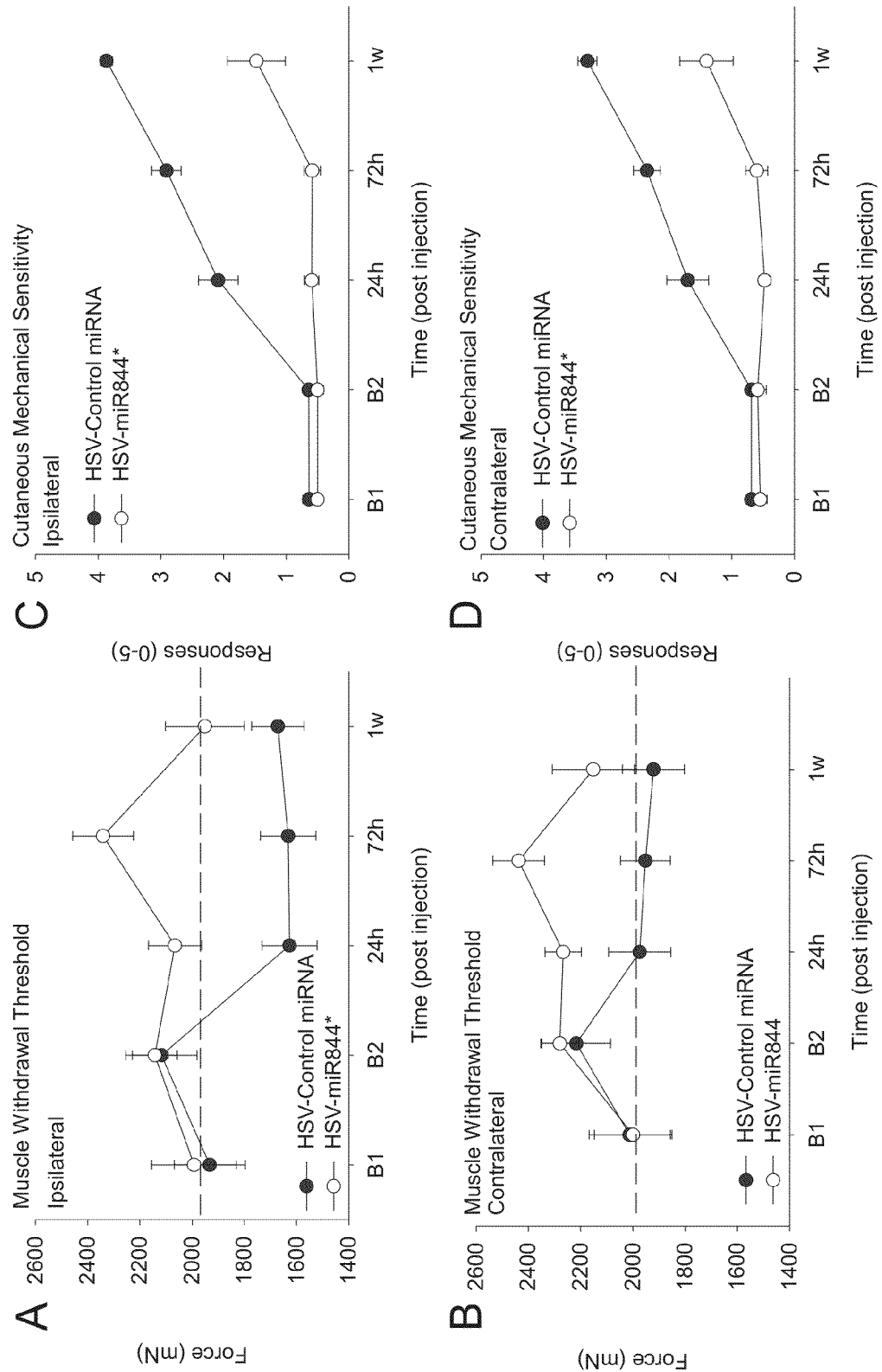
FIG. 19(A-D) are graphs showing that miR-ASIC3 prevents development of primary and secondary hyperalgesia in vivo. A and B) Primary hyperalgesia (muscle withdrawal thresholds) was measured in animals injected in the left gastrocnemius muscle with HSV recombinant viruses before (B1), 4 weeks after virus injection (B2), and 24 h, 72 h, and 1 week after carrageenan induced muscle inflammation. HSVmiR844 injected animals do not develop hyperalgesia at 24 h, 72 h, and 1 week after muscle inflammation (*, $p<0.05$ on the ipsilateral side). C and D) Secondary hyperalgesia (responses to repeated von Frey stimulation of the paw) was measured bilaterally and shows show that HSV-miR844 injected animals do not develop paw hyperalgesia 24 h, 72 h, and 1 week after muscle inflammation (*, $p<0.05$ on the ipsilateral and contralateral sides).

In CHO-K1 cells co-transfected with ASIC1a and ASIC3, miR-ASIC3 reduces the amplitude of acidic pH-evoked currents FIGS. 19. A and B) Primary hyperalgesia (muscle withdrawal thresholds) was measured in animals injected in the left gastrocnemius muscle with HSV recombinant viruses before (B1), 4 weeks after virus injection (B2), and 24 h, 72 h, and 1 week after carrageenan induced muscle inflammation. HSV-miR844 injected animals do not develop hyperalgesia at 24 h, 72 h, and 1 week after muscle inflammation (*, p<0.05 on the ipsilateral side). C and D) Secondary hyperalgesia (responses to repeated von Frey stimulation of the paw) was measured bilaterally and shows show that HSV-miR844 injected animals do not develop paw hyperalgesia 24 h, 72 h, and 1 week after muscle inflammation (*, p<0.05 on the ipsilateral and contralateral sides).

Figure 20:
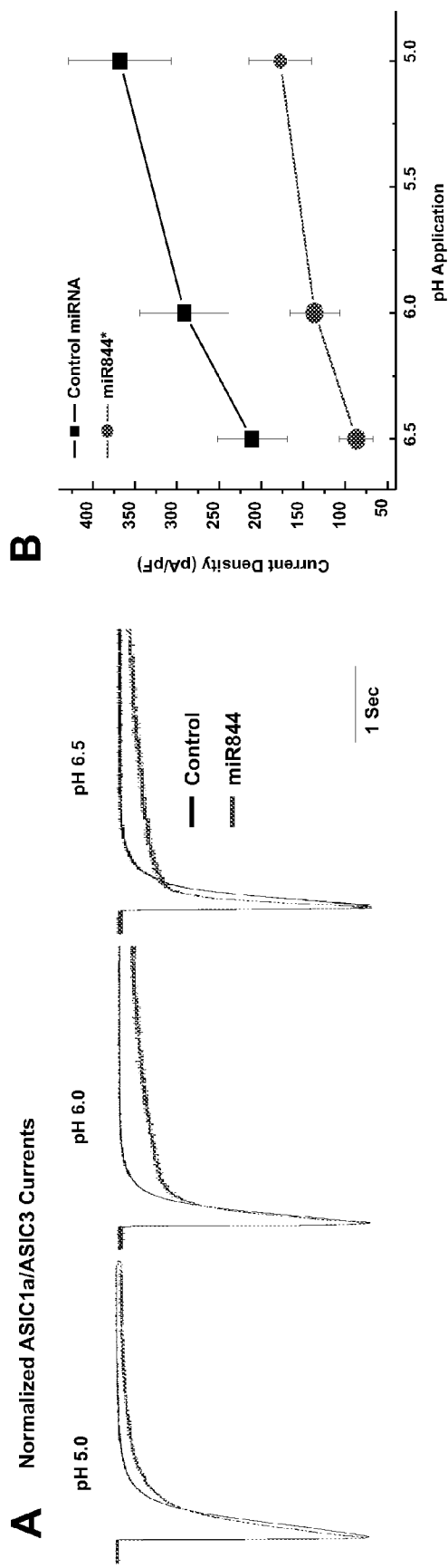
FIG. 20(A-B) are graphs showing that miR-ASIC3 inhibits ASIC1a/ASIC3 hetermoeric channels in CHO-K1 cells. A) Representative pH-evoked currents from CHO cells co-expressing both ASIC1a and ASIC3 (1:1 ratio) plus control miRNA (black traces) or miR844 (red traces). B) Mean current density from cells in part A evoked by the indicated pH solutions show that miR844 significantly inhibits the current density at all test pHs (*, $p<0.05$)

Specific down regulation of ASIC3 in the primary sensory neurons prevents the development of both primary and secondary hyperalgesia following muscle inflammation by reducing acid-evoked currents in the primary afferents innervating muscle. FIG. 20. A) Representative pH-evoked currents from CHO cells co-expressing both ASIC1a and ASIC3 (1:1 ratio) plus control miRNA (black traces) or miR844 (red traces). B) Mean current density from cells in part A evoked by the indicated pH solutions show that miR844 significantly inhibits the current density at all test pHs (*, p<0.05).

REFERENCES

1. Akopian A N, Chen C C, Ding Y, Cesare P Wood J N: A new member of the acid-sensing ion channel family. Neuroreport 11:2217-2222, 2000.
2. Allen N J Attwell D: Modulation of ASIC channels in rat cerebellar Purkinje neurons by ischaemia-related signals. J Physiol 543:521-529, 2002.
3. Alvarez de la Rosa D, Krueger S R, Kolar A, Shao D, Fitzsimonds R M Canessa C M: Distribution, subcellular localization and ontogeny of ASIC1 in the mammalian central nervous system. J Physiol 546:77-87, 2003.
4. Askwith C C, Cheng C, Ikuma M, Benson C, Price M P Welsh M J: Neuropeptide FF and FMRFamide potentiate acid-evoked currents from sensory neurons and proton-gated DEG/ENaC channels. Neuron 26:133-141, 2000.
5. Askwith C C, Wemmie J A, Price M P, Rokhlina T Welsh M J: Acid-sensing ion channel 2 (ASIC2) modulates ASIC1 H+-activated currents in hippocampal neurons. J Biol Chem 279:18296-18305, 2004.
6. Babinski K, Le K T Seguela P: Molecular cloning and regional distribution of a human proton receptor subunit with biphasic functional properties. J Neurochem 72:51-57, 1999.
7. Babinski K, Catarsi S, Biagini G Seguela P: Mammalian ASIC2a and ASIC3 subunits co-assemble into heteromeric proton-gated channels sensitive to Gd3+. J Biol Chem 275:28519-28525, 2000.
8. Baron A, Waldmann R Lazdunski M: ASIC-like, proton-activated currents in rat hippocampal neurons. J Physiol 539:485-494, 2002.
9. Baron A, Voilley N, Lazdunski M Lingueglia E: Acid sensing ion channels in dorsal spinal cord neurons. J Neurosci 28:1498-1508, 2008.
10. Bassilana F, Champigny G, Waldmann R, de Weille J R, Heurteaux C Lazdunski M: The acid-sensitive ionic channel subunit ASIC and the mammalian degenerin MDEG form a heteromultimeric H+-gated Na+ channel with novel properties. J Biol Chem 272:28819-28822, 1997.
11. Benson C J, Xie J, Wemmie J A, Price M P, Henss J M, Welsh M J Snyder P M: Heteromultimers of DEG/ENaC subunits form H+-gated channels in mouse sensory neurons. Proc Natl Acad Sci USA 99:2338-2343, 2002.
12. Bileviciute I, Stenfors C, Theodorsson E Lundeberg T: Unilateral injection of calcitonin gene-related peptide (CGRP) induces bilateral oedema formation and release of CGRP-like immunoreactivity in the rat hindpaw. Br J Pharmacol 125:1304-1312, 1998.
13. Carnally S M, Dev H S, Stewart A P, Barrera N P, Van Bemmelen M X, Schild L, Henderson R M Edwardson J M: Direct visualization of the trimeric structure of the ASIC1a channel, using AFM imaging. Biochem Biophys Res Commun 372:752-755, 2008.
14. Catarsi S, Babinski K Seguela P: Selective modulation of heteromeric ASIC proton-gated channels by neuropeptide FF. Neuropharmacology 41:592-600, 2001
15. Chen C C, England S, Akopian A N Wood J N: A sensory neuron-specific, proton-gated ion channel. Proc Natl Acad Sci USA 95:10240-10245, 1998.

16. Chen C C, Zimmer A, Sun W H, Hall J, Brownstein M J Zimmer A: A role for ASIC3 in the modulation of high-intensity pain stimuli. Proc Natl Acad Sci USA 99:8992-8997, 2002.
17. Chen X, Kalbacher H Grunder S: The tarantula toxin psalmotoxin 1 inhibits acid-sensing ion channel (ASIC) 1a by increasing its apparent H+ affinity. J Gen Physiol 126:71-79, 2005.
18. Chen X, Kalbacher H Grunder S: Interaction of acid-sensing ion channel (ASIC) 1 with the tarantula toxin psalmotoxin 1 is state dependent. J Gen Physiol 127:267-276, 2006.
19. Coryell M W, Ziemann A E, Westmoreland P J, Haenfler J M, Kurjakovic Z, Zha X M, Price M, Schnizler M K Wemmie J A: Targeting ASIC1a reduces innate fear and alters neuronal activity in the fear circuit. Biol Psychiatry 62:1140-1148, 2007.
20. Coscoy S, Lingueglia E, Lazdunski M Barbry P: The Phe-Met-Arg-Phe-amide-activated sodium channel is a tetramer. J Biol Chem 273:8317-8322, 1998.
21. Deval E, Noel J, Lay N, Alloui A, Diochot S, Friend V, Jodar M, Lazdunski M Lingueglia E: ASIC3, a sensor of acidic and primary inflammatory pain. EMBO J 27:3047-3055, 2008.
22. Drew L J, Rohrer D K, Price M P, Blaver K E, Cockayne D A, Cesare P Wood J N: Acid-sensing ion channels ASIC2 and ASIC3 do not contribute to mechanically activated currents in mammalian sensory neurones. J Physiol 556:691-710, 2004.
23. Duan B, Wu L J, Yu Y Q, Ding Y, Jing L, Xu L, Chen J Xu T L: Upregulation of acid-sensing ion channel ASIC1a in spinal dorsal horn neurons contributes to inflammatory pain hypersensitivity. J Neurosci 27:11139-11148, 2007.
24. Dube G R, Lehto S G, Breese N M, Baker S J, Wang X, Matulenko M A, Honore P, Stewart A O, Moreland R B Brioni J D: Electrophysiological and in vivo characterization of A-317567, a novel blocker of acid sensing ion channels. Pain 117:88-96, 2005.
25. Ferreira J, Santos A R Calixto J B: Antinociception produced by systemic, spinal and supraspinal administration of amiloride in mice. Life Sci 65:1059-1066, 1999.
26. Garcia-Anoveros J, Derfler B, Neville-Golden J, Hyman B T Corey D P: BNaC1 and BNaC2 constitute a new family of human neuronal sodium channels related to degenerins and epithelial sodium channels. Proc Natl Acad Sci USA 94:1459-1464, 1997.
27. Grunder S, Geissler H S, Bassler E L Ruppersberg J P: A new member of acid-sensing ion channels from pituitary gland. Neuroreport 11:1607-1611, 2000.
28. Häbler C: Untersuchungen zur Molekularpathologie der Gelenkexsudate and ihre klinischen Ergebnisse. Arch Klin Chir 156:20-42, 1929.
29. Hesselager M, Timmermann D B Ahring P K: pH Dependency and desensitization kinetics of heterologously expressed combinations of acid-sensing ion channel subunits. J Biol Chem 279:11006-11015, 2004.
30. Ikeuchi M, Kolker S J, Burnes L A, Walder R Y Sluka K A: Role of ASIC3 in the primary and secondary hyperalgesia produced by joint inflammation in mice. Pain 137:662-669, 2008.
31. Immke D C McCleskey E W: ASIC3: a lactic acid sensor for cardiac pain. ScientificWorldJournal 1:510-512, 2001.
32. Ishibashi K Marumo F: Molecular cloning of a DEG/ENaC sodium channel cDNA from human testis. Biochem Biophys Res Commun 245:589-593, 1998.
33. Jahr H, van Driel M, van Osch G J, Weinans H van Leeuwen J P: Identification of acid-sensing ion channels in bone. Biochem Biophys Res Commun 337:349-354, 2005.
34. Jasti J, Furukawa H, Gonzales E B Gouaux E: Structure of acid-sensing ion channel 1 at 1.9 A resolution and low pH. Nature 449:316-323, 2007.
35. Jensen K, Tuxen C, Pedersen-Bjergaard U Jansen I: Pain, tenderness, wheal and flare induced by substance-P, bradykinin and 5-hydroxytryptamine in humans. Cephalalgia 11:175-182, 1991.
36. Kelly S, Dunham J P Donaldson L F: Sensory nerves have altered function contralateral to a monoarthritis and may contribute to the symmetrical spread of inflammation. Eur J Neurosci 26:935-942, 2007.
37. Krishtal O: The ASICs: signaling molecules? Modulators? Trends Neurosci 26:477-483, 2003.
38. Leonard A S, Yermolaieva O, Hruska-Hageman A, Askwith C C, Price M P, Wemmie J A Welsh M J: cAMP-dependent protein kinase phosphorylation of the acid-sensing ion channel-1 regulates its binding to the protein interacting with C-kinase-1. Proc Natl Acad Sci USA 100:2029-2034, 2003.
39. Light A R, Hughen R W, Zhang J, Rainier J, Liu Z Lee J: Dorsal root ganglion neurons innervating skeletal muscle respond to physiological combinations of protons, ATP, and lactate mediated by ASIC, P2x, and TRPV1. J Neurophysiol 100:1184-1201, 2008.
40. Lingueglia E, de Weille J R, Bassilana F, Heurteaux C, Sakai H, Waldmann R Lazdunski M: A modulatory subunit of acid sensing ion channels in brain and dorsal root ganglion cells. J Biol Chem 272:29778-29783, 1997.
41. Lingueglia E: Acid-sensing ion channels in sensory perception. J Biol Chem 282:17325-17329, 2007.
42. Mamet J, Baron A, Lazdunski M Voilley N: Proinflammatory mediators, stimulators of sensory neuron excitability via the expression of acid-sensing ion channels. J Neurosci 22:10662-10670, 2002.
43. Mamet J, Lazdunski M Voilley N: How nerve growth factor drives physiological and inflammatory expressions of acid-sensing ion channel 3 in sensory neurons. J Biol Chem 278:48907-48913, 2003.
44. Mazzuca M, Heurteaux C, Alloui A, Diochot S, Baron A, Voilley N, Blondeau N, Escoubas P, Gelot A, Cupo A, Zimmer A, Zimmer A M, Eschalier A Lazdunski M: A tarantula peptide against pain via ASIC1a channels and opioid mechanisms. Nat Neurosci 10:943-945, 2007.
45. Mogil J S, Breese N M, Witty M F, Ritchie J, Rainville M L, Ase A, Abbadi N, Stucky C L Seguela P: Transgenic expression of a dominant-negative ASIC3 subunit leads to increased sensitivity to mechanical and inflammatory stimuli. J Neurosci 25:9893-9901, 2005.
46. Molliver D C, Immke D C, Fierro L, Pare M, Rice F L McCleskey E W: ASIC3, an acid-sensing ion channel, is expressed in metaboreceptive sensory neurons. Mol Pain 1:35, 2005.
47. O'Brien C, Woolf C J, Fitzgerald M, Lindsay R M Molander C: Differences in the chemical expression of rat primary afferent neurons which innervate skin, muscle or joint. Neuroscience 32:493-502, 1989.
48. Ohtori S, Inoue G, Koshi T, Ito T, Doya H, Saito T, Moriya H Takahashi K: Up-regulation of acid-sensing ion channel 3 in dorsal root ganglion neurons following application of nucleus pulposus on nerve root in rats. Spine 31:2048-2052, 2006.
49. Page A J, Brierley S M, Martin C M, Price M P, Symonds E, Butler R, Wemmie J A Blackshaw L A: Different contributions of ASIC channels 1a, 2, and 3 in gastrointestinal mechanosensory function. Gut 54:1408-1415, 2005.
50. Page A J, Brierley S M, Martin C M, Hughes P A Blackshaw L A: Acid sensing ion channels 2 and 3 are required for inhibition of visceral nociceptors by benzamil. Pain 133:150-160, 2007.
51. Pedersen-Bjergaard U, Nielsen L B, Jensen K, Edvinsson L, Jansen I Olesen J: Calcitonin gene-related peptide, neurokinin A and substance P: effects on nociception and neurogenic inflammation in human skin and temporal muscle. Peptides 12:333-337, 1991.
52. Plenderleith M B Snow P J: The plant lectin Bandeiraea simplicifolia I-B4 identifies a subpopulation of small diameter primary sensory neurones which innervate the skin in the rat. Neurosci Lett 159:17-20, 1993.
53. Poirot O, Berta T, Decosterd I Kellenberger S: Distinct ASIC currents are expressed in rat putative nociceptors and are modulated by nerve injury. J Physiol 576:215-234, 2006.
54. Price M P, Snyder P M Welsh M J: Cloning and expression of a novel human brain Na+ channel. J Biol Chem 271: 7879-7882, 1996.
55. Price M P, Lewin G R, McIlwrath S L, Cheng C, Xie J, Heppenstall P A, Stucky C L, Mannsfeldt A G, Brennan T J, Drummond H A, Qiao J, Benson C J, Tarr D E, Hrstka R F, Yang B, Williamson R A Welsh M J: The mammalian sodium channel BNC1 is required for normal touch sensation. Nature 407:1007-1011, 2000.
56. Price M P, McIlwrath S L, Xie J, Cheng C, Qiao J, Tarr D E, Sluka K A, Brennan T J, Lewin G R Welsh M J: The DRASIC cation channel contributes to the detection of cutaneous touch and acid stimuli in mice. Neuron 32:1071-1083, 2001.
57. Rees H, Sluka K A, Westlund K N Willis W D: The role of glutamate and GABA receptors in the generation of dorsal root reflexes by acute arthritis in the anaesthetized rat. J Physiol 484 (Pt 2):437-445, 1995.
58. Rees H, Sluka K A, Lu Y, Westlund K N Willis W D: Dorsal root reflexes in articular afferents occur bilaterally in a chronic model of arthritis in rats. J Neurophysiol 76:4190-4193, 1996.
59. Roza C, Puel J L, Kress M, Baron A, Diochot S, Lazdunski M Waldmann R: Knockout of the ASIC2 channel in mice does not impair cutaneous mechanosensation, visceral mechanonociception and hearing. J Physiol 558:659-669, 2004.
60. Salinas M, Rash L D, Baron A, Lambeau G, Escoubas P Lazdunski M: The receptor site of the spider toxin PcTx1 on the proton-gated cation channel ASIC1a. J Physiol 570: 339-354, 2006.
61. Skyba D A, Radhakrishnan R Sluka K A: Characterization of a method for measuring primary hyperalgesia of deep somatic tissue. J Pain 6:41-47, 2005.
62. Sluka K A, Radhakrishnan R, Price M P, Welsh M J: ASIC3 Mediates Mechanical Hyperalgesia Induced by Muscle Injury, in Brune K, Handwerker H O (eds): Hyperalgesia: molecular mechanisms and clinical implications. Seattle, IASP Press, 2004, pp 105-112.
63. Sluka K A Westlund K N: Behavioral and immunohistochemical changes in an experimental arthritis model in rats. Pain 55:367-377, 1993.
64. Sluka K A, Rees H, Westlund K N Willis W D: Fiber types contributing to dorsal root reflexes induced by joint inflammation in cats and monkeys. J Neurophysiol 74:981-989, 1995.
65. Sluka K A, Price M P, Breese N M, Stucky C L, Wemmie J A Welsh M J: Chronic hyperalgesia induced by repeated acid injections in muscle is abolished by the loss of ASIC3, but not ASIC1. Pain 106:229-239, 2003.
66. Sluka K A, Radhakrishnan R, Benson C J, Eshcol J O, Price M P, Babinski K, Audette K M, Yeomans D C Wilson S P: ASIC3 in muscle mediates mechanical, but not heat, hyperalgesia associated with muscle inflammation. Pain 129:102-112, 2007.
67. Sluka K A, Westlund-High K N: Neurologic regulation of inflammation, in Firestein G S, Budd R C, Harris E D, Jr., McInnes I B, Ruddy S, Sergent J S (eds): Kelley's textbook of rheumatology, eighth edition. Philadelphia, Pa., Saunders/Elsevier, 2009, pp 411-419.
68. Staniland A A McMahon S B: Mice lacking acid-sensing ion channels (ASIC) 1 or 2, but not ASIC3, show increased pain behaviour in the formalin test. Eur J Pain, 2008.
69. Ugawa S, Ueda T, Takahashi E, Hirabayashi Y, Yoneda T, Komai S Shimada S: Cloning and functional expression of ASIC-beta2, a splice variant of ASIC-beta. Neuroreport 12:2865-2869, 200.
70. Ugawa S, Ueda T, Ishida Y, Nishigaki M, Shibata Y Shimada S: Amiloride-blockable acid-sensing ion channels are leading acid sensors expressed in human nociceptors. J Clin Invest 110:1185-1190, 2002.
71. Voilley N, de Weille J, Mamet J Lazdunski M: Nonsteroid anti-inflammatory drugs inhibit both the activity and the inflammation-induced expression of acid-sensing ion channels in nociceptors. J Neurosci 21:8026-8033, 2001.
72. Voilley N: Acid-sensing ion channels (ASICs): new targets for the analgesic effects of non-steroid anti-inflammatory drugs (NSAIDs). Curr Drug Targets Inflamm Allergy 3:71-79, 2004.
73. Waldmann R, Champigny G, Voilley N, Lauritzen I Lazdunski M: The mammalian degenerin MDEG, an amiloride-sensitive cation channel activated by mutations causing neurodegeneration in Caenorhabditis elegans. J Biol Chem 271:10433-10436, 1996.
74. Waldmann R, Bassilana F, de Weille J, Champigny G, Heurteaux C Lazdunski M: Molecular cloning of a noninactivating proton-gated Na+ channel specific for sensory neurons. J Biol Chem 272:20975-20978, 1997.
75. Wall P D Woolf C J: Muscle but not cutaneous C-afferent input produces prolonged increases in the excitability of the flexion reflex in the rat. J Physiol 356:443-458, 1984.
76. Wemmie J A, Chen J, Askwith C C, Hruska-Hageman A M, Price M P, Nolan B C, Yoder P G, Lamani E, Hoshi T, Freeman J H, Jr Welsh M J: The acid-activated ion channel ASIC contributes to synaptic plasticity, learning, and memory. Neuron 34:463-477, 2002.
77. Wemmie J A, Askwith C C, Lamani E, Cassell M D, Freeman J H, Jr Welsh M J: Acid-sensing ion channel 1 is localized in brain regions with high synaptic density and contributes to fear conditioning. J Neurosci 23:5496-5502, 2003.
78. Wemmie J A, Price M P Welsh M J: Acid-sensing ion channels: advances, questions and therapeutic opportunities. Trends Neurosci 29:578-586, 2006.
79. Woolf C J Wall P D: Relative effectiveness of C primary afferent fibers of different origins in evoking a prolonged facilitation of the flexor reflex in the rat. J Neurosci 6:1433-1442, 1986.
80. Wu L J, Duan B, Mei Y D, Gao J, Chen J G, Zhuo M, Xu L, Wu M Xu T L: Characterization of acid-sensing ion channels in dorsal horn neurons of rat spinal cord. J Biol Chem 279:43716-43724, 2004.
81. Yen Y T, Tu P H, Chen C J, Lin Y W, Hsieh S T Chen C C: Role of acid-sensing ion channel 3 in sub-acute-phase inflammation. Mol Pain 5:1, 2009.

What is claimed is:

1. An isolated oligonucleotide comprising a polynucleotide sequence comprising about 12 to 25 nucleotides in length sufficiently complementary to a microRNA target sequence of ASIC3, wherein the oligonucleotide is capable of decreasing ASIC3 expression or activity, wherein the isolated oligonucleotide comprises a polynucleotide sequence obtained from SEQ ID NOS:1-4, 6-16 or 21 or its complement.

2. An isolated oligonucleotide comprising a polynucleotide sequence comprising about 12 to 25 nucleotides in length sufficiently complementary to a microRNA target sequence of ASIC3, wherein the oligonucleotide is capable of decreasing ASIC3 expression or activity, wherein microRNA target sequence of ASIC3 is the sequence of SEQ ID NO:5, 17, 18, 19, or 20 or a complement thereof.

3. An isolated single stranded microRNA molecule, said molecule comprising the sequence of bases identified in SEQ ID NOS:1, 2, 4, 5, 8, 11, 14, 17-27 or the complement thereof wherein the molecule is capable of decreasing ASIC3 expression or activity.

* * * * *